US009096862B2

(12) United States Patent
Xiao et al.

(10) Patent No.: US 9,096,862 B2
(45) Date of Patent: Aug. 4, 2015

(54) ENHANCING DROUGHT TOLERANCE AND BACTERIAL RESISTANCE OF CROP SPECIES BY FUNCTIONAL INTERFERENCE OF 14-3-3

(75) Inventors: Shunyuan Xiao, Rockville, MD (US); Wenming Wang, Chengdu (CN); Xiaohua Yang, Ardmore, OK (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 593 days.

(21) Appl. No.: 13/340,833

(22) Filed: Dec. 30, 2011

(65) Prior Publication Data
US 2012/0198585 A1 Aug. 2, 2012

Related U.S. Application Data

(60) Provisional application No. 61/428,882, filed on Dec. 31, 2010, provisional application No. 61/452,282, filed on Mar. 14, 2011.

(51) Int. Cl.
| | |
|---|---|
| *C12N 15/82* | (2006.01) |
| *C07K 14/415* | (2006.01) |
| *C07K 19/00* | (2006.01) |
| *C12N 15/62* | (2006.01) |

(52) U.S. Cl.
CPC .......... *C12N 15/8218* (2013.01); *C07K 14/415* (2013.01); *C12N 15/62* (2013.01); *C12N 15/8273* (2013.01); *C12N 15/8281* (2013.01); *C07K 2319/70* (2013.01); *C07K 2319/85* (2013.01)

(58) Field of Classification Search
None
See application file for complete search history.

(56) References Cited

U.S. PATENT DOCUMENTS

| 7,910,801 B2 | 3/2011 | Xiao et al. | |
| 2007/0214517 A1* | 9/2007 | Alexandrov et al. | 800/278 |
| 2010/0251430 A1* | 9/2010 | Ryu et al. | 800/298 |

FOREIGN PATENT DOCUMENTS

WO WO2010117750 10/2010

OTHER PUBLICATIONS

Cockrell et al. 14-3-3 proteins.Wiley Encyclopedia of Chemical Biology. 2009. pp. 1-9.*
Baunsgaard, L., et al., The 14-3-3 proteins associate with the plant plasma membrane H(+)-ATPase to generate a fusicoccin binding complex and a fusicoccin responsive system. Plant J, 1998. 13(5): p. 661-71.
Buckley, T.N. (2005). The control of stomata by water balance. New Phytol 168, 275-292.
Crossway, A.; Oakes, J.; Irvine, J.; Ward, B.; Knauf, V.; Shewmaker, C.K. 1986. Integration of foreign DNA following microinjection of tobacco meophyll photoplasts. *Mol. Gen. Genet.*, 202: 179-85.
Dong, S., Kang, S., Lonial, S., Khoury, H.J., Viallet, J., and Chen, J. (2008). Targeting 14-3-3 sensitizes native and mutant BCR-ABL to inhibition with U0126, rapamycin and Bcl-2 inhibitor GX15-070. Leukemia 22, 572-577.

(Continued)

*Primary Examiner* — Anne Kubelik
*Assistant Examiner* — Ashley K Buran
(74) *Attorney, Agent, or Firm* — Marianne Fuierer; Moore & Van Allen, PLLC

(57) ABSTRACT

The present invention generally relates to plants and methods of producing modified plants that exhibit enhanced drought resistance and bacterial resistance relative to non-modified plants.

16 Claims, 8 Drawing Sheets

(56) References Cited

OTHER PUBLICATIONS

Figure 1:
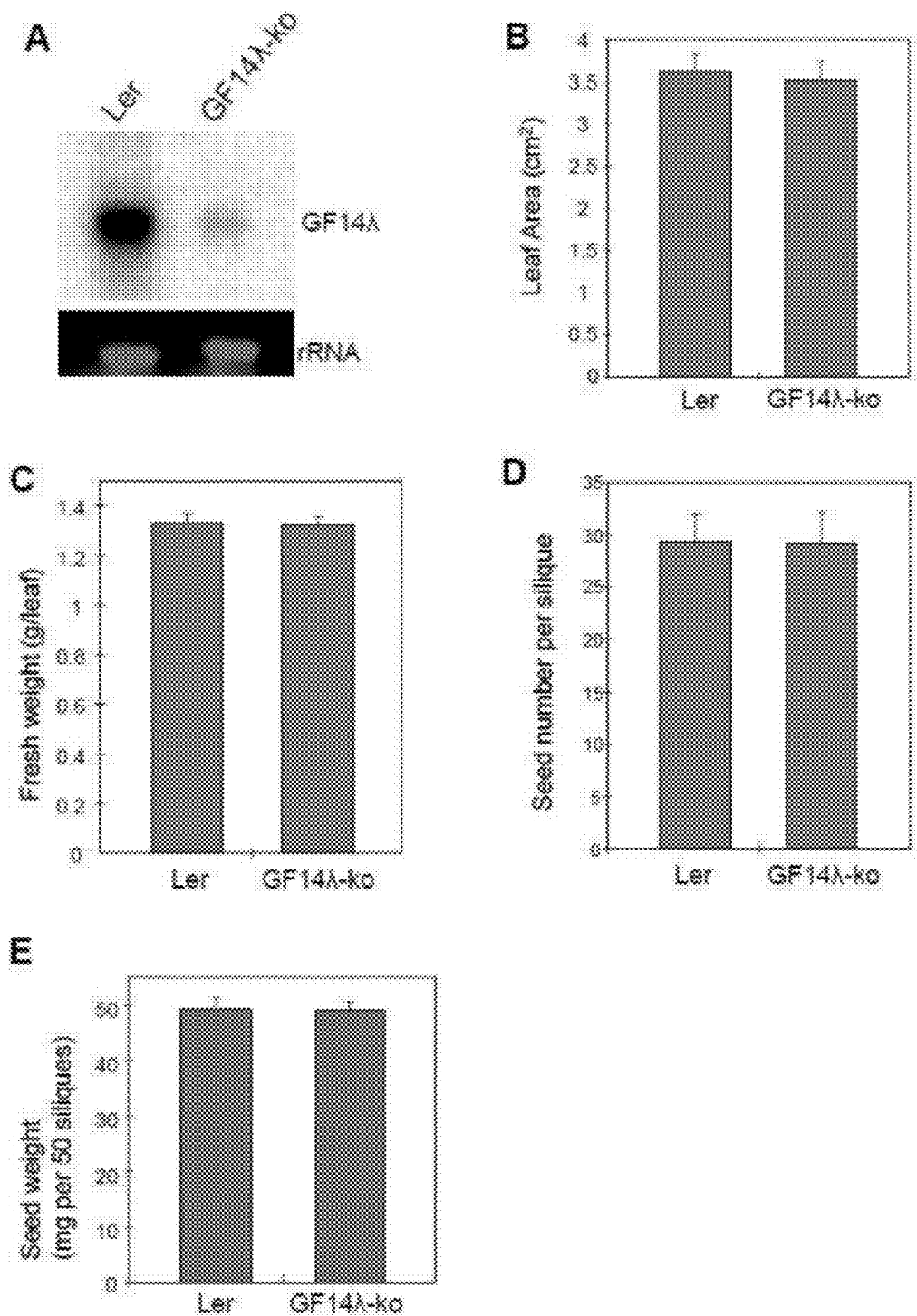

Dong, S., Kang, S., Gu, T.L., Kardar, S., Fu, H., Lonial, S., Khoury, H.J., Khuri, F., and Chen, J. (2007). 14-3-3 Integrates prosurvival signals mediated by the AKT and MAPK pathways in ZNF198-FGFR1-transformed hematopoietic cells. Blood 110, 360-369.

Fraley R. T., Dellaporta S. L., and Papahadjopoulos D. (1982) Liposome-Mediated Delivery of Tobacco Mosaic Virus RNA into Tobacco Protoplasts: A Sensitive Assay for Monitoring Liposome-Protoplast Interactions. *Proc. Natl. Acad. Sci. USA*, 79(6):1859-1863.

Fromm M., Taylor L. P., and Walbot V. (1985) Expression of genes transferred into monocot and dicot plant cells by electroporation. *Proc. Natl Acad. Sci. USA*, 82(17):5824-5828.

Fuglsang, A.T., et al., (2003) The binding site for regulatory 14-3-3 protein in plant plasma membrane H+-ATPase: involvement of a region promoting phosphorylation-independent interaction in addition to the phosphorylation-dependent C-terminal end. J Biol Chem, 278(43): p. 42266-72.

Hashimoto, M., Negi, J., Young, J., Israelsson, M., Schroeder, J.I., and Iba, K. (2006). *Arabidopsis* HT1 kinase controls stomatal movements in response to CO2. Nat Cell Biol 8, 391-397.

Jahn, T., et al., (1997) The 14-3-3 protein interacts directly with the C-terminal region of the plant plasma membrane H(+)-ATPase. Plant Cell, 9(10): p. 1805-14.

Kinoshita, T., and Shimazaki, K. (1999). Blue light activates the plasma membrane H(+)-ATPase by phosphorylation of the C-terminus in stomatal guard cells. Embo J 18, 5548-5558.

Kinoshita, T., Emi, T., Tominaga, M., Sakamoto, K., Shigenaga, A., Doi, M., and Shimazaki, K. (2003). Blue-light- and phosphorylation-dependent binding of a 14-3-3 protein to phototropins in stomatal guard cells of broad bean. Plant Physiol 133, 1453-1463.

Kinoshita, T. and K. Shimazaki, (2002) Biochemical evidence for the requirement of 14-3-3 protein binding in activation of the guard-cell plasma membrane H+-ATPase by blue light. Plant Cell Physiol, 43(11): p. 1359-65.

Klein T. M., Wolf E. D., Wu R. and Sanford J. C. (1987) High-velocity microprojectiles for delivering nucleic acids into living cells. *Nature*, 327(6117):70-73.

Korthout, H.A. and H.A. de Boer, (1994) A fusicoccin binding protein belongs to the family of 14-3-3 brain protein homologs. Plant Cell, 6(11): p. 1681-92.

Krens F. A, Molendijk L., Wullems G. J. and Schilperoort R. A. (1982) In vitro transformation of plant protoplasts with Ti-plasmid DNA. *Nature*, 296(5852):72-74.

Li, J., Gong, X., Lin, H., Song, Q., Chen, J., and Wang, X. (2005). DGP1, a drought-induced guard cell-specific promoter and its function analysis in tobacco plants. Sci China C Life Sci 48, 181-186.

Melotto, M., Underwood, W., Koczan, J., Nomura, K., and He, S.Y. (2006). Plant stomata function in innate immunity against bacterial invasion. Cell 126, 969-980.

Odell J. T., Nagy F. and Chua N.-H.. (1985). Identification of DNA sequences required for activity of the cauliflower mosaic virus 35S promoter. *Nature.* 313(6005):810-812.

Ottmann, C., et al., (2007) Structure of a 14-3-3 coordinated hexamer of the plant plasma membrane H+-ATPase by combining X-ray crystallography and electron cryomicroscopy. Mol Cell, 25(3): p. 427-40.

Paul, A.L., Sehnke, P.C., and Ferl, R.J. (2005). Isoform-specific subcellular localization among 14-3-3 proteins in *Arabidopsis* seems to be driven by client interactions. Mol Biol Cell 16, 1735-1743.

Petosa, C., et al., (1998) 14-3-3zeta binds a phosphorylated Raf peptide and an unphosphorylated peptide via its conserved amphipathic groove. J Biol Chem, 273(26): p. 16305-10.

Schell J., (1987) Transgenic plants as tools to study the molecular organization of plant genes. *Science,* 237(4819):1176-1183.

Shimazaki, K., Doi, M., Assmann, S.M., and Kinoshita, T. (2007). Light regulation of stomatal movement. Annu Rev Plant Biol 58, 219-247.

Wang, B., Yang, H., Liu, Y.C., Jelinek, T., Zhang, L., Ruoslahti, E., and Fu, H. (1999). Isolation of high-affinity peptide antagonists of 14-3-3 proteins by phage display. Biochemistry 38, 12499-12504.

Xiao, S., Ellwood, S., Calis, O., Patrick, E., Li, T., Coleman, M., and Turner, J.G. (2001). Broad-spectrum mildew resistance in *Arabidopsis thaliana* mediated by RPW8. Science 291, 118-120.

\* cited by examiner

SEQUENCE LISTING

<160> NUMBER OF SEQ ID NOS: 20

<210> SEQ ID NO 1
<211> LENGTH: 20
<212> TYPE: PRT
<213> ORGANISM: Artificial Sequence
<220> FEATURE:
<223> OTHER INFORMATION: Synthetic Construct

<400> SEQUENCE: 1

Pro His Cys Val Pro Arg Asp Leu Ser Trp Leu Asp Leu Glu Ala Asn
1               5                   10                  15

Met Cys Leu Pro
            20

<210> SEQ ID NO 2
<211> LENGTH: 59
<212> TYPE: PRT
<213> ORGANISM: Artificial Sequence
<220> FEATURE:
<223> OTHER INFORMATION: Synthetic Construct

<400> SEQUENCE: 2

Ala Val Asn Ile Phe Pro Glu Lys Gly Ser Tyr Arg Glu Leu Ser Glu
1               5                   10                  15

Ile Ala Glu Gln Ala Lys Arg Arg Ala Glu Ile Ala Arg Leu Arg Glu
            20                  25                  30

Leu His Thr Leu Lys Gly His Val Glu Ser Val Val Lys Leu Lys Gly
        35                  40                  45

Leu Asp Ile Glu Thr Pro Ser His Tyr Asp Val
    50                  55

<210> SEQ ID NO 3
<211> LENGTH: 60
<212> TYPE: DNA
<213> ORGANISM: Artificial Sequence
<220> FEATURE:
<223> OTHER INFORMATION: Synthetic Construct

<400> SEQUENCE: 3
ccgcattgcg tgccgcgcga tctgagctgg ctggatctgg aagcgaacat gtgcctgccg        60

<210> SEQ ID NO 4
<211> LENGTH: 238
<212> TYPE: PRT
<213> ORGANISM: Artificial Sequence
<220> FEATURE:
<223> OTHER INFORMATION: Synthetic Construct

<400> SEQUENCE: 4

```
Met Lys Leu Ala Ser Ser Glu Asn Val Ile Thr Glu Phe Met Arg Phe
1               5                   10                  15

Lys Val Arg Met Glu Gly Thr Val Asn Gly His Glu Phe Glu Ile Glu
            20                  25                  30

Gly Glu Gly Glu Gly Arg Pro Tyr Glu Gly His Asn Thr Val Lys Leu
        35                  40                  45

Lys Val Thr Lys Gly Gly Pro Leu Pro Phe Ala Trp Asp Ile Leu Ser
50                  55                  60

Pro Gln Phe Gln Tyr Gly Ser Lys Val Tyr Val Lys His Pro Ala Asp
65                  70                  75                  80

Ile Pro Asp Tyr Lys Lys Leu Ser Phe Pro Glu Gly Phe Lys Trp Glu
                85                  90                  95

Arg Val Met Asn Phe Glu Asp Gly Gly Val Ala Thr Val Thr Gln Asp
            100                 105                 110

Ser Ser Leu Gln Asp Gly Cys Phe Ile Tyr Lys Val Lys Phe Ile Gly
        115                 120                 125

Val Asn Phe Pro Ser Asp Gly Pro Val Met Gln Lys Lys Thr Met Gly
130                 135                 140

Trp Glu Ala Ser Thr Glu Arg Leu Tyr Pro Arg Asp Gly Val Leu Lys
145                 150                 155                 160

Gly Glu Thr His Lys Ala Leu Lys Leu Lys Asp Gly Gly His Tyr Leu
                165                 170                 175

Val Glu Phe Lys Ser Ile Tyr Met Ala Lys Lys Pro Val Gln Leu Pro
            180                 185                 190

Gly Tyr Tyr Tyr Val Asp Ala Lys Leu Asp Ile Thr Ser His Asn Glu
        195                 200                 205

Asp Tyr Thr Ile Val Glu Gln Tyr Glu Arg Thr Glu Gly Arg His His
    210                 215                 220

Leu Phe Leu Arg Ser Arg Ala Pro Pro Pro Pro Leu Thr
225                 230                 235
```

<210> SEQ ID NO 5
<211> LENGTH: 2802
<212> TYPE: DNA
<213> ORGANISM: Artificial Sequence
<220> FEATURE:
<223> OTHER INFORMATION: Synthetic Construct

<400> SEQUENCE: 5

```
ttataagacg agctcattg tcgctcgtca gcgggttgat gctgaaactt cctattgtgg      60
gtttgtatgc ctcctcccgt ccgacctgag cgttaaaatc tccgataact atctgcacat     120
gggcagcaga tgtgctccat ctccaactgc gtatagaaga tctccgtctc gtcatcggag     180
tttccaaggt gcggactgta cacattaata atgctgaggt tgaagaacct gccacggatt     240
cttagcctgc acattcgctc attgatcgat caccatccga tcacccactt tcgcatctcc     300
cctatgatca ggaacaccga accgagctca tgcttttcaa cccctgctct ggtagattat     360
gcagtcactg cgatggaggc gctccgaaac cccttttccag cgcaactctt gtagtgctac    420
```

```
tatttcgaag ccgtcctcgt ccataagaat gcgggtgctt tcaggtgccg tgagtgatct    480
gcagttccat gtctcgagtt tccaatcgtg tgttttgttt cgcagcattg gtctataatc    540
gttgaatccg attcgaaact tcatggtttt cgatcgttgc gtttatattg agggaggctt    600
gcaaggctgc ttccccgaca cctcatctcg tcggagggac ccgtaggaca ggagggacga    660
ccagccgccc ctaacaagga gaacagaggc tagctatccc cctccactca atttagccat    720
atcacccatc ttcccaaggg attgggtttt cacgtttacc caagctcaga tatttggaga    780
gacatgttac cattctatac gccgggaacg tattgaattg aagtgaggtg gagagtctat    840
gttaatcttc aagaggcttc ggatccatac tatatacaat atgagagatg gttttcataa    900
tattgggaaa aattcatctg agcatctcca tctcaaacgc agcttaggaa ggacaaagct    960
aagatgtctc aaagacgtat ttgaagtact ggggactata catgtctgtc agtccagcat   1020
cgtccgcggc ggacaagtat tttgaagtgg agaactttct catgaccagt tgacagccag   1080
cacaactcaa catcaatgtt ggtgtcggac ttgattttg atccctgata agtgagtttt   1140
gaacgatttc aaagatacga tcacctcgcc caagttggtg gttttcggcc cctttaactt   1200
caacccgagg ctaagtgccg atcgctcgat cctttggaaa gctaggatag aagagcctca   1260
aaccaatgat gtctatgtca tctatgtttg gtgcggatac accgccagtg aaacaagtgt   1320
aataagaata aactttgatt atttaatatt ttttacctt cgcataatgt atttgacgaa   1380
cttaccatga tttatatctg ttggcaaaat gagacaattt attcatgttc tgcgtatact   1440
ttaatgatca tcgtattgca acatgcttgt ttaaccatta tttatcaaac attacttttc   1500
tctctacttg tgcacagtaa agcaggtgcc atttgcttaa cactaacaaa agctgtacaa   1560
atactgggga cggttccgag gtccgacgat cgtccgagtt ttcccttata aaagcgccgc   1620
gatcgtaacg taaagatcat cagtagaatt tgctcttttc cacagttcac aggtgaataa   1680
acgatgaagc ttgcctcctc cgagaacgtc atcaccgagt tcatgcgctt caaggtgcgc   1740
atggagggca ccgtgaacgg ccacgagttc gagatcgagg gcgagggcga gggccgcccc   1800
tacgagggcc acaacaccgt gaagctgaag gtgaccaagg gcggcccccct gcccttcgcc   1860 tgggacatcc tgtcccccca gttccagtac ggctccaagg tgtacgtgaa gcaccccgcc   1920
gacatccccg actacaagaa gctgtccttc cccgagggct tcaagtggga gcgcgtgatg   1980
aacttcgagg acggcggcgt ggcgaccgtg acccaggact cctccctgca ggacggctgc   2040
ttcatctaca aggtgaagtt catcggcgtg aacttcccct ccgacggccc cgtgatgcag   2100
aagaagacca tgggctggga ggcctccacc gagcgcctgt accccgcga cggcgtgctg   2160 aagggcgaga cccacaaggc cctgaagctg aaggacggcg gccactacct ggtggagttc   2220
aagtccatct acatggccaa gaagcccgtg cagctgcccg gctactacta cgtggacgcc   2280
aagctggaca tcacctccca caacgaggac tacaccatcg tggagcagta cgagcgcacc   2340
gagggccgcc accacctgtt cctgagatct cgagcaccac caccaccacc actaacctag   2400
gtagctgagc gcatgcgatc tcggcttcaa aacggtactg gattttggat tcaaacgaaa   2460
gccatcgcta caacagaaca aataaaagaa cattaatcaa aacgcataaa agatgggtta   2520
attgtattca ataaggagaa aagtaattcc tactagatag tttactatca cgcgaaagga   2580
tggccagtct tcactacggg aagacaacct cgctgggaat cgaaactctg tcaacgctgg   2640
aggtgccaac acatcttcgt aataaacatt tttacattta tccaggcgta agaaacacg   2700 atttagttat caatttgtat ttttggttct tatgaagaat aaacttcttc aaattcactt   2760
ccacgaatat tccgtcccgt tccgccagtt ccattcgagc tc                        2802
```

```
<210> SEQ ID NO 6
<211> LENGTH: 884
<212> TYPE: DNA
<213> ORGANISM: Artificial Sequence
<220> FEATURE:
<223> OTHER INFORMATION: Synthetic Construct

<400> SEQUENCE: 6
gtcaacatgg tggagcacga cacacttgtc tactccaaaa atatcaaaga tacagtctca      60
gaagaccaaa gggcaattga acttttcaa caaagggtaa tatccggaaa cctcctcgga     120
ttccattgcc cagctatctg tcactttatt gtgaagatag tggaaaagga aggtggctcc     180
tacaaatgcc atcattgcga taaggaaag gccatcgttg aagatgcctc tgccgacagt     240
ggtcccaaag atggaccccc acccacgagg agcatcgtgg aaaagaaga cgttccaacc     300
acgtcttcaa gcaagtggat tgatgtgat aacatggtgg agcacgacac acttgtctac     360
tccaaaaata tcaaagatac agtctcagaa gaccaaaggg caattgagac ttttcaacaa     420
agggtaatat ccggaaacct cctcggattc cattgcccag ctatctgtca ctttattgtg     480
aagatagtgg aaaaggaagg tggctcctac aaatgccatc attgcgataa aggaaaggcc     540
atcgttgaag atgcctctgc cgacagtggt cccaaagatg gaccccacc cacgaggagc     600
atcgtggaaa agaagacgt tccaaccacg tcttcaaagc aagtggattg atgtgatatc     660
tccactgacg taagggatga cgcacaatcc cactatcctt cgcaagaccc ttcctctata     720
taaggaagtt catttcattt ggagaggacc tcgacctcaa cacaacatat acaaaacaaa     780
cgaatctcaa gcaatcaagc attctacttc tattgcagca atttaaatca tttcttttaa     840
agcaaaagca attttctgaa aattttcacc atttacgaac gata                      884

<210> SEQ ID NO 7
<211> LENGTH: 178
<212> TYPE: DNA
<213> ORGANISM: Artificial Sequence
<220> FEATURE:
<223> OTHER INFORMATION: Synthetic Contruct

<400> SEQUENCE: 7
gctgttaaca tcttccctga gaaaggaagt tacagagaat tgtctgagat cgctgagcaa      60
gctaagagaa gagctgagat cgctagctta gggagctgca cactcaag ggacatgtgg       120
aatcagtcgt gaagctaaag ggcttggaca ttgaaactcc cagtcactac gacgtgta      178

<210> SEQ ID NO 8
<211> LENGTH: 720
<212> TYPE: DNA
<213> ORGANISM: Artificial Sequence
<220> FEATURE:
<223> OTHER INFORMATION: Synthetic Construct

<400> SEQUENCE: 8
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccacct tcggctacgg cctgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
```

```
aaccgcatcg agctgaaggg catcgacttc aaggaggacg gcaacatcct ggggcacaag    420
ctggagtaca actacaacag ccacaacgtc tatatcatgg ccgacaagca gaagaacggc    480
atcaaggtga acttcaagat ccgccacaac atcgaggacg gcagcgtgca gctcgccgac    540
cactaccagc agaacacccc catcggcgac ggccccgtgc tgctgcccga caaccactac    600
ctgagctacc agtccgccct gagcaaagac cccaacgaga gcgcgatca catggtcctg     660 ctggagttcg tgaccgccgc cgggatcact ctcggcatgg acgagctgta caagtccgga    720
```

<210> SEQ ID NO 9
<211> LENGTH: 513
<212> TYPE: DNA
<213> ORGANISM: Artificial Sequence
<220> FEATURE:
<223> OTHER INFORMATION: Synthetic Construct

<400> SEQUENCE: 9

```
caccaagctt gagaaggatg tgccgtttgt tataataaac agccacacga cgtaaacgta     60
aaatgaccac atgatgggcc aatagacatg gaccgactac taataatagt aagttacatt    120
ttaggatgga ataaatatca taccgacatc agtttgaaag aaaagggaaa aaagaaaaaa    180
ataaataaaa gatatactac cgacatgagt tccaaaaagc aaaaaaaaag atcaagccga    240
cacagacacg cgtagagagc aaatcctaga agtaggcaag tagcaatgtc acattcttaa    300
agctaaatgc ttttcaaaa gaatcacaat aaagaaacac ttgacccgtg tatcacccca     360
actacttctt caactacatc ctctatatat aaacacgcta aaataacta gttagtattt     420 ttaaatatta cacattgcct ttccaagaaa ctcgaaaaat taaataaaa aaccacatca     480 acaaaaaaga agcagcaata tataatagga tcc                                 513
```

<210> SEQ ID NO 10
<211> LENGTH: 330
<212> TYPE: PRT
<213> ORGANISM: Artificial Sequence
<220> FEATURE:
<223> OTHER INFORMATION: Synthetic Construct

<400> SEQUENCE: 10

```
Met Pro His Cys Val Pro Arg Asp Leu Ser Trp Leu Asp Leu Glu Ala
1               5                   10                  15

Asn Met Cys Leu Pro Gly Gly Ser Gly Gly Gly Gly Gly Gly Thr Val
            20                  25                  30

Ser Lys Gly Glu Glu Leu Phe Thr Gly Val Val Pro Ile Leu Val Glu
        35                  40                  45

Leu Asp Gly Asp Val Asn Gly His Lys Phe Ser Val Ser Gly Glu Gly
    50                  55                  60

Glu Gly Asp Ala Thr Tyr Gly Lys Leu Thr Leu Lys Phe Ile Cys Thr
65                  70                  75                  80

Thr Gly Lys Leu Pro Val Pro Trp Pro Thr Leu Val Thr Thr Phe Gly
                85                  90                  95

Tyr Gly Leu Gln Cys Phe Ala Arg Tyr Pro Asp His Met Lys Gln His
            100                 105                 110

Asp Phe Phe Lys Ser Ala Met Pro Glu Gly Tyr Val Gln Glu Arg Thr
        115                 120                 125

Ile Phe Phe Lys Asp Asp Gly Asn Tyr Lys Thr Arg Ala Glu Val Lys
    130                 135                 140

Phe Glu Gly Asp Thr Leu Val Asn Arg Ile Glu Leu Lys Gly Ile Asp
145                 150                 155                 160
```

```
Phe Lys Glu Asp Gly Asn Ile Leu Gly His Lys Leu Glu Tyr Asn Tyr
            165                 170                 175

Asn Ser His Asn Val Tyr Ile Met Ala Asp Lys Gln Lys Asn Gly Ile
        180                 185                 190

Lys Val Asn Phe Lys Ile Arg His Asn Ile Glu Asp Gly Ser Val Gln
    195                 200                 205

Leu Ala Asp His Tyr Gln Gln Asn Thr Pro Ile Gly Asp Gly Pro Val
210                 215                 220

Leu Leu Pro Asp Asn His Tyr Leu Ser Tyr Gln Ser Ala Leu Ser Lys
225                 230                 235                 240

Asp Pro Asn Glu Lys Arg Asp His Met Val Leu Leu Glu Phe Val Thr
                245                 250                 255

Ala Ala Gly Ile Thr Leu Gly Met Asp Glu Leu Tyr Lys Ser Gly Ala
            260                 265                 270

Val Asn Ile Phe Pro Glu Lys Gly Ser Tyr Arg Glu Leu Ser Glu Ile
        275                 280                 285

Ala Glu Gln Ala Lys Arg Arg Ala Glu Ile Ala Arg Leu Arg Glu Leu
    290                 295                 300

His Thr Leu Lys Gly His Val Glu Ser Val Val Lys Leu Lys Gly Leu
305                 310                 315                 320

Asp Ile Glu Thr Pro Ser His Tyr Asp Val
                325                 330

<210> SEQ ID NO 11
<211> LENGTH: 993
<212> TYPE: DNA
<213> ORGANISM: Artificial Sequence
<220> FEATURE:
<223> OTHER INFORMATION: Synthetic Construct

<400> SEQUENCE: 11
atgccgcatt gcgtgccgcg cgatctgagc tggctggatc tggaagcgaa catgtgcctg      60
ccgggaggta gtggtggagg aggaggtggt accgtgagca agggcgagga gctgttcacc     120
ggggtggtgc ccatcctggt cgagctggac ggcgacgtaa acggccacaa gttcagcgtg     180
tccggcgagg gcgagggcga tgccacctac ggcaagctga ccctgaagtt catctgcacc     240
accggcaagc tgcccgtgcc ctggcccacc ctcgtgacca ccttcggcta cggcctgcag     300
tgcttcgccc gctaccccga ccacatgaag cagcacgact tcttcaagtc cgccatgccc     360
gaaggctacg tccaggagcg caccatcttc ttcaaggacg acggcaacta caagacccgc     420
gccgaggtga agttcgaggg cgacaccctg gtgaaccgca tcgagctgaa gggcatcgac     480
ttcaaggagg acggcaacat cctggggcac aagctggagt acaactacaa cagccacaac     540
gtctatatca tggccgacaa gcagaagaac ggcatcaagg tgaacttcaa gatccgccac     600
aacatcgagg acggcagcgt gcagctcgcc gaccactacc agcagaacac ccccatcggc     660
gacggccccg tgctgctgcc cgacaaccac tacctgagct accagtccgc cctgagcaaa     720
gaccccaacg agaagcgcga tcacatggtc ctgctggagt tcgtgaccgc cgccgggatc     780
actctcggca tggacgagct gtacaagtcc ggagctgtta acatcttccc tgagaaagga     840
agttacagag aattgtctga ggtcgctgag caagctaaga aagagctga gatcgctagg     900 cttagggagc tgcacacact caagggacat gtggaatcag tcgtgaagct aaagggcttg     960
gacattgaaa ctcccagtca ctacgacgtg tag                                  993
```

<210> SEQ ID NO 12
<211> LENGTH: 273
<212> TYPE: PRT
<213> ORGANISM: Artificial Sequence
<220> FEATURE:
<223> OTHER INFORMATION: Synthetic Construct

<400> SEQUENCE: 12

```
Met Ala Ala Thr Leu Gly Arg Asp Gln Tyr Val Tyr Met Ala Lys Leu
1               5                   10                  15

Ala Glu Gln Ala Glu Arg Tyr Glu Glu Met Val Gln Phe Met Glu Gln
            20                  25                  30

Leu Val Thr Gly Ala Thr Pro Ala Glu Glu Leu Thr Val Glu Glu Arg
        35                  40                  45

Asn Leu Leu Ser Val Ala Tyr Lys Asn Val Ile Gly Ser Leu Arg Ala
    50                  55                  60

Ala Trp Arg Ile Val Ser Ser Ile Glu Gln Lys Glu Glu Ser Arg Lys
65                  70                  75                  80

Asn Asp Glu His Val Ser Leu Val Lys Asp Tyr Arg Ser Lys Val Glu
                85                  90                  95

Ser Glu Leu Ser Ser Val Cys Ser Gly Ile Leu Lys Leu Leu Asp Ser
            100                 105                 110

His Leu Ile Pro Ser Ala Gly Ala Ser Glu Ser Lys Val Phe Tyr Leu
        115                 120                 125

Lys Met Lys Gly Asp Tyr His Arg Tyr Met Ala Glu Phe Lys Ser Gly
    130                 135                 140

Asp Glu Arg Lys Thr Ala Ala Glu Asp Thr Met Leu Ala Tyr Lys Ala
145                 150                 155                 160

Ala Gln Asp Ile Ala Ala Ala Asp Met Ala Pro Thr His Pro Ile Arg
                165                 170                 175

Leu Gly Leu Ala Leu Asn Phe Ser Val Phe Tyr Tyr Glu Ile Leu Asn
            180                 185                 190

Ser Ser Asp Lys Ala Cys Asn Met Ala Lys Gln Ala Phe Glu Glu Ala
        195                 200                 205

Ile Ala Glu Leu Asp Thr Leu Gly Glu Glu Ser Tyr Lys Asp Ser Thr
    210                 215                 220

Leu Ile Met Gln Leu Leu Arg Asp Asn Leu Thr Leu Trp Thr Ser Asp
225                 230                 235                 240

Met Gln Thr Asn Gln Met His His Ile Arg Asp Ile Lys Glu His Val
                245                 250                 255

Lys Thr Glu Ile Thr Ala Lys Pro Cys Val Leu Ser Tyr Tyr Tyr Ser
            260                 265                 270

Met
```

<210> SEQ ID NO 13
<211> LENGTH: 1040
<212> TYPE: DNA
<213> ORGANISM: Artificial Sequence
<220> FEATURE:
<223> OTHER INFORMATION: Synthetic Construct

<400> SEQUENCE: 13

```
ccacgcgtcc gccattaaac aaaaaaaaat caaatctctc tctttctctc tctaatggcg    60
gcgacattag cagagaccca gtatgtgtac atggcgaagc tcgccgagca ggcggagcgt   120
tacgaagaga tggttcaatt catggaacag ctcgttacag cgctactcca gcggaagag   180 ctcaccgttg aagagaggaa tctcctctct gttgcttaca aaaacgtgat cggatctcta   240
```

```
cgcgccgcct ggaggatcgt gtcttcgatt gagcagaagg aagagagtag gaagaacgac        300
gagcacgtgt cgcttgtcaa ggattacaga tctaaagttg agtctgagct ttcttctgtt        360
tgctctggaa tccttaagct ccttgactcg catctgatcc catctgctgg agcgagtgag        420
tctaaggtct tttacttgaa gatgaaaggt gattatcatc ggtacatggc tgagtttaag        480
tctggtgatg agaggaaaac tgctgctgaa gataccatgc tcgcttacaa agcagctcag        540
gatatcgcag ctgcggatat ggcacctact catccgataa ggcttggtct ggccctgaat        600
ttctcagtgt tctactatga gattctcaat tcttcagaca aagcttgtaa catggccaaa        660
caggcttttg aggaggccat agctgagctt gacactctgg gagaggaatc ctacaaagac        720
agcactctca taatgcagtt gctgagggac aatttaaccc tttggacctc cgatatgcag        780
gagcagatgg acgaggcctg aggatctaga tgaaggggg gagggttgtt acgcgatgtt         840
tctgccacca aatcgatctc aaaatcccca taacctttgc tcaaaaactg tgaaaaaga        900 ttgaagtgtt tatgatgatt atgattgtgc acagcttgat gatttatcta ctctactaaa        960
cctctgtgct cttaatattt attgtctcga ctctgctcaa gccttaaaaa catctttctc       1020
cttaaaaaaa aaaaaaaaaa                                                   1040

<210> SEQ ID NO 14
<211> LENGTH: 253
<212> TYPE: DNA
<213> ORGANISM: Artificial Sequence
<220> FEATURE:
<223> OTHER INFORMATION: Synthetic Construct

<400> SEQUENCE: 14
gagaaggatg tgccgtttgt tataataaac agccacacga cgtaaacgta aaatgaccac         60
atgatgggcc aatagacatg gaccgactac taataatagt aagttacatt ttaggatgga        120
ataaatatca taccgacatc agtttgaaag aaaagggaaa aaaagaaaaa ataaataaaa        180
gatatactac cgacatgagt tccaaaaagc aaaaaaaaag atcaagccga cacagacacg        240
cgtagagagc aaa                                                           253

<210> SEQ ID NO 15
<211> LENGTH: 241
<212> TYPE: DNA
<213> ORGANISM: Artificial Sequence
<220> FEATURE:
<223> OTHER INFORMATION: Synthetic Construct

<400> SEQUENCE: 15
tagaagtagg caagtagcaa tgtcacattc ttaaagctaa atgcttttc aaaagaatca         60 caataaagaa acacttgacc cgtgtatcac cccaactact tcttcaacta catcctctat        120
atataaacac gctaaaaata actagttagt attttttaaat attacacatt gcctttccaa       180
gaaactcgaa aaattaaaat aaaaaaccac atcaacaaaa aagaagcagc aatatataat       240
a                                                                        241

<210> SEQ ID NO 16
<211> LENGTH: 241
<212> TYPE: PRT
<213> ORGANISM: Artificial Sequence
<220> FEATURE:
<223> OTHER INFORMATION: Synthetic Construct

<400> SEQUENCE: 16
```

```
Thr Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Gly Gly Ser Gly Gly Gly Gly Gly
1               5

<210> SEQ ID NO 18
<211> LENGTH: 97
<212> TYPE: DNA
<213> ORGANISM: Artificial Sequence
<220> FEATURE:
<223> OTHER INFORMATION: Synthetic Construct

<400> SEQUENCE: 18
caccatgccg cattgcgtgc cgcgcgatct gagctggctg gatctggaag cgaacatgtg     60
cctgccggga ggtagtggtg gaggaggagg tggtacc                             97

<210> SEQ ID NO 19
<211> LENGTH: 276
<212> TYPE: DNA
<213> ORGANISM: Artificial Sequence
```

-continued

```
<220> FEATURE:
<223> OTHER INFORMATION: Synthetic Construct

<400> SEQUENCE: 19
gctgttaaca tcttccctga gaaaggaagt tacagagaat tgtctgagat cgctgagcaa     60
gctaagagaa gagctgagat cgctaggtaa taaatccgat cacacacgat tctttttaat    120
ctaagtgtat ttttttgtgg gaattaaaca ctaattgaat tgttatatgt taaacaggct    180
tagggagctg cacacactca agggacatgt ggaatcagtc gtgaagctaa agggcttgga    240
cattgaaact cccagtcact acgacgtgta ggatcc                              276

<210> SEQ ID NO 20
<211> LENGTH: 253
<212> TYPE: DNA
<213> ORGANISM: Artificial Sequence
<220> FEATURE:
<223> OTHER INFORMATION: Synthetic Construct

<400> SEQUENCE: 20
cgttcaaaca tttggcaata aagtttctta agattgaatc ctgttgccgg tcttgcgatg     60
attatcatat aatttctgtt gaattacgtt aagcatgtaa taattaacat gtaatgcatg    120
acgttattta tgagatgggt ttttatgatt agagtcccgc aattatacat ttaatacgcg    180
atagaaaaca aaatatagcg cgcaaactag gataaattat cgcgcgcggt gtcatctatg    240
ttactagatc ggg                                                       253
```

ENHANCING DROUGHT TOLERANCE AND BACTERIAL RESISTANCE OF CROP SPECIES BY FUNCTIONAL INTERFERENCE OF 14-3-3

CROSS-REFERENCE TO RELATED APPLICATIONS

The present application claims priority to U.S. Provisional Patent Application No. 61/428,882 filed on Dec. 31, 2010 and U.S. Provisional Patent Application No. 61/452,282 filed on Mar. 14, 2011, the contents of both which are hereby incorporated by reference herein for all purposes.

GOVERNMENT INTEREST

This invention was made with government support under Grant Number 2005-35319-15656. The government has certain rights in the invention.

BACKGROUND OF THE INVENTION

Drought is perhaps the single most important factor that devastates crop production on the planet every year. Global warming aggravates this kind of natural disasters. Thus, breeding for drought-tolerant crop cultivars has never been as urgent as today. In general there are two ways to enhance drought tolerance of plants, that being, increasing water-absorbing ability or improving water-conservation power of plants.

Plants have evolved sophisticated mechanisms to cope with and adapt to the changing environment. For example, stomata opening/closing of plants is essential for water transpiration and gas exchange that are necessary for photosynthesis and is tightly regulated via multiple pathways to help plants constantly adjust to regular and irregular environmental changes such as light, water, $CO_2$ and pathogens (Melotto et al., 2006) (Shimazaki et al., 2007) (Hashimoto et al., 2006) (Buckley, 2005). Notably, U.S. Pat. No. 6,720,477 provides a method of increasing drought resistance and this is accomplished by overexpressing two 14-3-3 genes from *Physcomitrella patens* in *Arabidopsis thaliana* to enhanced drought tolerance.

Thus, it would be advantageous to understand the molecular basis of the regulatory mechanisms to help design strategies to create drought-tolerant and pathogen-resistant crop cultivars through engineering key regulators of stomata functions such that plants' responses to imminent drought stress or bacterial invasion can be pre-programmed and strengthened in a more controllable manner.

SUMMARY OF THE INVENTION

The mechanism of stomatal opening and closing controls gas exchange and limits water loss via evapo-transpiration, which is regulated by several interconnected molecular pathways. In daytime, (blue) light activates the proton pump ($H^+$-ATPase) at the plasma membrane (PM) of the guard cells, pumping $H^+$ out of the cell and establishing an electrochemical gradient across the PM, (ii) the membrane-potential-coupled ATP hydrolysis then allows $K^+$ to enter the guard cells, (iii) water follows the ions in, turgor increases, resulting in stomatal opening for gas exchange. It is conceivable that although plants have evolved complex mechanisms to close their stomata to conserve water under extreme drought conditions, they may do better if the proton pump can be shut down earlier or more completely during drought. Thus, the present invention relates to a method for sequestering 14-3-3s in the cytoplasm of guard cells during drought which can promote stomatal closure, thereby enhancing drought tolerance of plants.

The present invention, therefore, relates to isolated polynucleotides, polypeptides encoded thereby, and the use of those sequences for making transgenic plants with enhanced drought tolerance. The present invention also relates to processes for increasing the growth potential in plants under abnormal water conditions, recombinant nucleic acid molecules and polypeptides used for these processes and their uses, as well as to plants themselves, wherein the plant, or plants derived from the plant, plant cell, plant material or seed of a plant, has increased drought tolerance as compared to a wild-type plant cultivated under identical conditions.

In another aspect, the present invention provides a DNA construct that interferes with the 14-3-3 binding to the C-terminus of the proton pump ($H^+$-ATPase) at the plasma membrane of the guard cells and thus interferes with the activation of the proton pump and thus reduces the induction of the stomatal opening, wherein the DNA construct encodes for the R18 amino acid sequence of PHCVPRDLSWLDLEANMCLP (SEQ ID NO: 1), Yellow Fluorescence Protein (YFP) (providing a visual marker for expression), and the C-terminus of the proton pump (the binding site of 14-3-3) (SEQ ID NO: 2).

The present invention generally relates to plants and methods of producing modified plants that exhibit enhanced drought resistance and bacterial resistance relative to non-modified plants. Specifically the present invention relates to interacting with 14-3-3s, members of a highly conserved protein family, to prevent the 14-3-3 proteins from binding and activating the proton pump thus shutting down the protein pump and promoting stomatal closure.

In one aspect, the present invention relates to a method of enhancing drought tolerance and bacterial resistance of crop species, the method comprising interfering with expression of plant 14-3-3 genes or isoforms thereof and/or introducing coding for an expressed protein with binding affinity for the expressed 14-3-3 proteins.

In another aspect, the present invention provides a DNA construct that encodes for proteins that interfere with the 14-3-3 binding to the C-terminus of the proton pump ($H^+$-ATPase) at the plasma membrane of the guard cells, and thus, interferes with the activation of the proton pump thereby reducing the induction of the stomatal opening, wherein the DNA construct encodes for the R18 amino acid sequence of PHCVPRDLSWLDLEANMCLP (SEQ ID NO: 1), Yellow Fluorescence Protein (YFP) for providing a visual marker for expression (SEQ ID NO: 16), and the C-terminus of the proton pump, preferably the CT59 protein sequence of the *Arabidopsis* H+ ATPase (SEQ ID NO: 2) (the binding site of 14-3-3).

In yet another aspect, the DNA construct, along with a synthetic promoter, is introduced into a plant that expresses a 14-3-3 protein and wherein expression of the DNA construct confers guard cell specific expression of the 14-3-3 trapping protein, and exhibits significantly enhanced drought tolerance. Notably, because 14-3-3s are highly conserved in all plants, the same DNA construct can be used to engineer drought-tolerance in any plant species.

In another aspect, the present invention relates to a modified plant wherein the plant's 14-3-3 genes, isoforms or expressed 14-3-3 proteins are inhibited or interfered with to reduce stomatal aperture and/or its function in the plant.

In yet another aspect, the present invention relates to a modified plant wherein the plant's 14-3-3 genes, isoforms or expressed 14-3-3 proteins are inhibited or interfered with thereby regulating the control of stomatal open/closure to provide for reduced disease symptoms by limiting the entry of bacteria.

Figure 8:
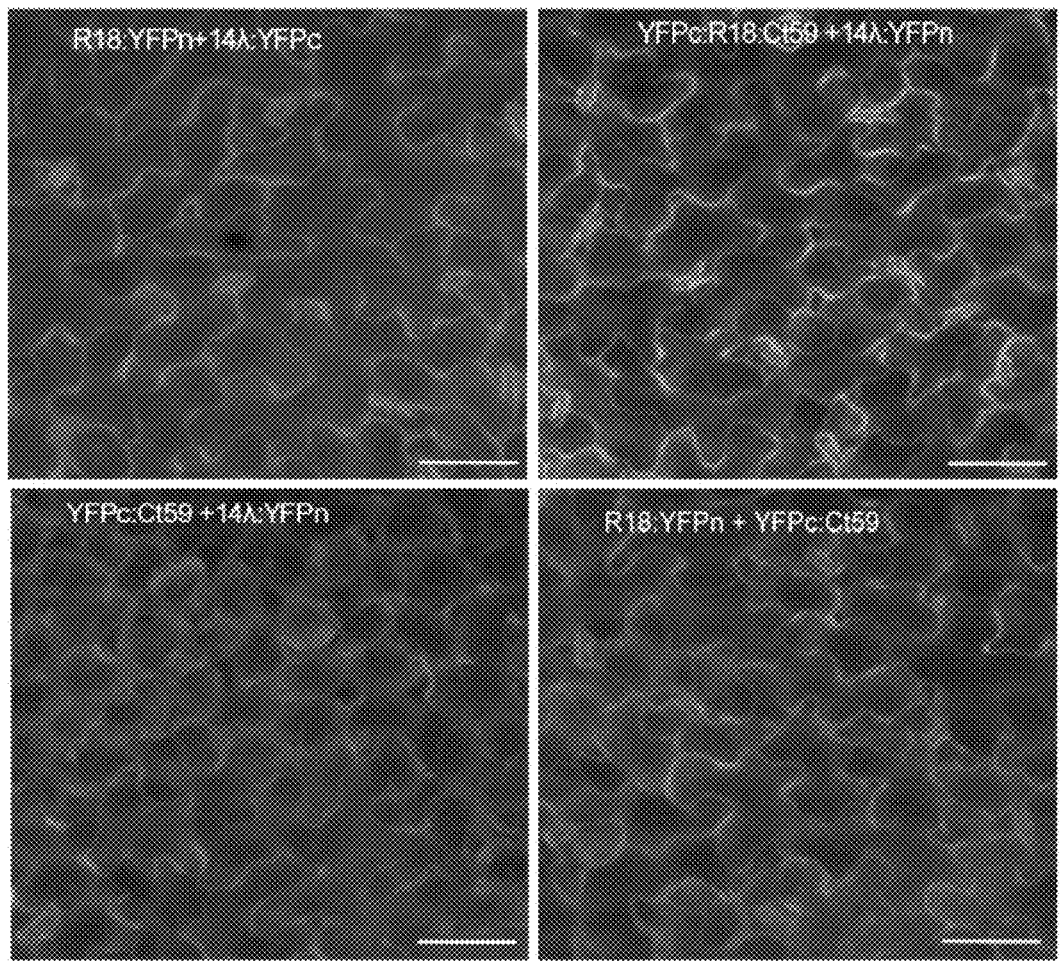

In a still further aspect, the present invention relates to a method of enhancing drought tolerance and bacterial resistance of a crop species, the method comprising:

expressing a short protein, R 18 (SEQ ID NO:1), in guard cells that bind to 14-3-3 proteins or isoforms thereof in the guard cell and wherein the short protein is expressed in combination with drought/bacterium-inducible guard cell-specific promoters, such as KST1, DGP1 or pGC. Preferably, the R18 is also expressed with Ct59, the C-terminal 59 amino acids of the *Arabidopsis* H+ ATPase (SEQ ID NO: 2) (as found in AT4G30190).

In yet another aspect, the present invention relates to method of enhancing drought tolerance and bacterial resistance of crop species, the method comprising:

silencing GF14λ and its crop orthologs by RNAi along with a drought/bacterium-inducible and guard cell-specific promoters.

In another aspect, the present invention provides for a composition comprising at least one modulator that binds, modulates or inhibits 14-3-3 proteins or isoforms thereof. Preferably the modulator is an iRNA agent that inhibits expression of 14-3-3 proteins or isoforms thereof and more preferably inhibits the expression of GF14λ.

In yet another aspect, the present invention provides for a composition including a chimeric binding protein that modulates activity of 14-3-3 proteins or isoforms thereof, wherein the chimeric binding protein comprises at least SEQ ID NO: 1 and SEQ ID NO: 2 or sequences having at least 80% identity thereof and has the functional activity to bind to and modulate the activity of 14-3-3s or isoforms thereof.

A still further aspect of the present invention provides for a method of enhancing drought tolerance and bacterial resistance of crop species, the method comprising the steps of:

(a) transforming plant cells with a recombinant DNA construct comprising a polynucleotide sequence which comprises nucleotide sequences encoding amino acid sequences comprising SEQ ID NO: 1 and 2 or having at least 90% identity thereof; and wherein the nucleotide sequence is operably linked to a promoter;

(b) regenerating transgenic plants from said transformed plant cells; and (c) selecting a transformed plant from said transgenic plants which exhibits increase in tolerance to drought stress as compared to an untransformed plant of the same species.

Other features and advantages of the invention will be apparent from the following detailed description, drawings and claims.

BRIEF DESCRIPTION OF THE FIGURES

FIG. 1 shows that GF14λ-ko plants exhibit normal growth and development. (A) Northern analysis of GF14λ mRNA levels in Landsberg erecta (Ler) wild type and GF14λ-ko leaf tissues. About 2 μg of total RNA was gel blotted and probed with GE14λ. The faint band in GF14λ may represent mRNA of GF14κ (At5g65430), which shows >85% nucleotide sequence identity with GF14λ. (B)-(E) Measurement of leaf area (B) and average fresh weight per leaf (C) (5-days-old full expanded mature leaves of 6 week-old plants, n=30), and average seed number per silique (D; n=15) and seed weight per 50 siliques (E; n=50). These experiments were repeated twice with similar results.

FIG. 2 shows GF14λ-ko plants that show enhanced bacterial resistance when spray-inoculated. (A) & (B) GE14λ-ko plants were as susceptible as Ler plants to *P. syringae* pv. Tomato DC3000 when infiltrated a bacterial suspension (−$10^6$cfu). (C) & (D) GF14λko plants showed enhanced resistance to *P. syringae* pv. Tomato DC3000 (Ps) when sprayed-inoculated with a bacterial suspension (−$10^8$cfu). 10 mM MgC12 was used as mock inoculation. The growth of bacteria was measure at 4 dpi. These experiments were repeated 3 times with similar results. Pictures were taken at 4 dpi.

FIG. 3 shows that GF14λ-ko plants exhibited reduced stomatal aperture and enhanced tolerance to drought. (A) & (B) GF14λ-ko plants had reduced stomatal aperture. Fully expanded leaves of 5 week-old GF14λ-ko and Ler plants were examined in day-time under DIC and the average stomatal aperture was calculated by measuring >30 stomatas. (C) Four week-old GE14λ-ko and Ler plants were kept in a growth chamber (set to 8 hrs light/16 hrs dark, 125 $\mu mol \cdot m^{-2} \cdot sec^{-1}$ light intensity, 28° C., and 50% relative humidity) without water supply for 14 days. Pictures were taken either at day 10 or day 15 (one day after ample water supply). (D) Fully-expanded mature leaves of 5 week-old plants of Ler and GF14λ-ko were detached and kept under the same conditions as for the whole plant-treatment. Water-loss rate was calculated as an average reduction of fresh weight of 8 detached leaves of three duplicated samples. All the experiments were repeated twice with similar results.

FIG. 4 shows that the expression of DsRed:R18 results in higher sensitivity to drought. (A) Transgenic *Arabidopsis* plants carrying the 35S::DsRed-R18 construct were examined under an eipfluorescent microscopy. DsRed:R18 was found to be preferentially expressed in the guard cells (white arrows). Bars=100 μm. (B) *Arabidopsis* plants overexpressing (OE) DsRed:R18 lose water more quickly than Col-0 wild-type plants. Detached mature leaves from plants of Col-0, and transgenic plants with a very high level (R18-OE) or a very low level (R18-NE) of DsRed:R18 (assessed using fluorescence from DsRed) were used for water loss assays under light or dark conditions. Experiments were repeated three times with similar results. Data shown are means±SE from one experiment.

FIG. 5 shows that the expression of R18:YFP:Ct59 in *Arabidopsis* results in enhanced drought tolerance. (A) Representative confocal images showing guard cell-specific expression of R18:YFP:Ct59 in *Arabidopsis* plants transgenic for 35SDG::R18-YFP-Ct59. Chloroplasts are visualized red due to autofluorescence. (B) Enhanced drought tolerance of one representative *Arabidopsis* line (R18-YFP-Ct59 #11) in comparison with the Col-g1 wild-type. Six week-old plants were kept in a growth chamber without watering for 14 days. (C) Detached mature leaves from plants of Col-g1, and two lines transgenic for 35S-DG::R18-YFP-Ct59 were used for water loss assays. Data shown are means±SE from one of three independent experiments.

FIG. 6 shows that plants transgenic for 355-DG::R18-YFP-Ct59 show no obvious difference in plant growth and development. Three representative plants (10 weeks-old) were shown.

FIG. 7 shows the In planta interaction of the indicated proteins revealed by BiFC. Respective DNA constructs were transiently co-expressed in *N. benthamiana* by agroinfiltration. Green indicates (brighter outlines) YFP signal; red indicates autofluorescence from chloroplasts. Representative Z-stack (30×0.1 μm) confocal images were shown. Bar=50 μm FIG. 8 shows the interaction of the indicated proteins revealed by BiFC in stable transgenic *Arabidopsis* plants expressing the indicated DNA constructs. Green indicates (brighter outlines) YFP signal; red indicates autofluorescence from chlorophyll as the background. Bar=50 µm

DESCRIPTION OF THE INVENTION

Following long-standing patent law convention, the terms "a" and "an" mean "one or more" when used in this application, including the claims.

The term "promoter," as used herein refers to a region of DNA upstream from the structural gene and involved in recognition and binding RNA polymerase and other proteins to initiate transcription. A "plant promoter" is a promoter capable of initiating transcription in plant cells. An "inducible" promoter is a promoter which is under more precise environmental or developmental control. Examples of environmental conditions that may effect transcription by inducible promoters include anaerobic conditions or the presence of light.

The term "plant," as used herein, includes whole plants, plant organs (e.g., leaves, stems, roots, etc.), seeds and plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The term "expression," as used herein, refers to the transcription and translation of a gene so that a protein is synthesized.

The term "antisense orientation," as used herein, refers to the orientation of nucleic acid sequence from a gene that is inserted in an expression cassette in an inverted manner with respect to its naturally occurring orientation.

The term "operably linked," as used herein, refers to functional linkage between a promoter and a second sequence, wherein the promoter sequence initiates transcription of RNA corresponding to the second sequence.

The terms "cells," "host cells" or "recombinant host cells," as used herein, are used interchangeably and mean not only to the particular subject cell, but also to the progeny or potential progeny of such a cell. Because certain modifications can occur in succeeding generations due to either mutation or environmental influences, such progeny might not, in fact, be identical to the parent cell, but are still included within the scope of the term as used herein.

The term "modified," as used herein, means an alteration in a nucleotide or amino acid sequence which includes adding or removing discrete amino acid residues or nucleotide units. The term "modified" encompasses detectable labels as well as those entities added as aids in purification.

The terms "modulate", "modulating", and "modulator," as used herein, are meant to be construed to encompass inhibiting, blocking, agonizing, antagonizing, or otherwise affecting 14-3-3 activity in plants and specifically guard cells.

The term "mutation," as used herein, carries its traditional connotation and means a change, inherited, naturally occurring or introduced, in a nucleic acid or polypeptide sequence, and is used in its sense as generally known to those of skill in the art.

The term "polypeptide," as used herein, refers to peptides, polypeptides and proteins, unless otherwise noted. As used herein, the terms "protein," "polypeptide" and "peptide" are used interchangeably herein when referring to a gene product.

The term "polynucleotide," as used herein, means a sequence of nucleotides connected by phosphodiester linkages. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U). A polynucleotide of the present invention can be prepared using standard techniques well known to one of skill in the art.

The term "complementary sequence," as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

The term "gene," as used herein, refers broadly to any segment of DNA associated with a biological function. A gene encompasses sequences including but not limited to a coding sequence, a promoter region, a cis-regulatory sequence, a non-expressed DNA segment is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "gene expression," as used herein, refers to the process of converting genetic information encoded in a gene into RNA (e.g., mRNA, rRNA, tRNA, or snRNA) through "transcription" of a deoxyribonucleic gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (ie., RNA or protein), while "down-regulation" or "repression" refers to regulation that decrease production. Molecules (e.g., transcription factors) that are involved in up-regulation or down-regulation are often called "activators" and "repressors," respectively.

The term "identity," as used herein means that a polynucleotide or polypeptide comprises a sequence that has at least 80% sequence identity, preferably at least 90% or more preferably at least 97%, compared to a reference sequence over a comparison window.

The term "inhibit" or "inhibiting," as used herein, means that a response is decreased or prevented due to the presence of an interfering nucleotide sequence or an interfering protein.

The term "analog," as used herein means any inhibiting polypeptide having an amino acid residue sequence substantially identical to a sequence of the natural ligand of the 14-3-3 in which one or more residues have been conservatively substituted with a functionally similar residue and which displays the 14-3-3 modulator inhibiting activity as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

The term, "conservative substitution," as used herein includes the use of a chemically derivatized residue in place of a non-derivatized residue provided that such polypeptide displays the requisite inhibition activity.

The term "chemical derivative," as used herein, refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as chemical derivatives are those peptides which contain one or more naturally occurring amino acid derivatives of the twenty standard amino acids. For examples: 4-hydroxyproline can be substituted for proline; 5-hydroxylysine can be substituted for lysine; 3-methylhistidine can be substituted for histidine; homoserine can be substituted for serine; and ornithine can be substituted for lysine. Polypeptides of the present invention also include any polypeptide having one or more additions and/or deletions or residues relative to the sequence of a polypeptide whose sequence is shown herein, so long as the requisite activity is maintained.

The term "fragment," as used herein mean any subject polypeptide having an amino acid residue sequence shorter than that of a polypeptide disclosed herein.

General Methods

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., 1989.

One embodiment of an interfering nucleotide sequence is a nucleic acid that is antisense to a nucleic acid that expresses 14-3-3 or isoforms thereof. For example, an antisense nucleic acid (e.g. DNA) may be introduced into cells in vitro or in vivo. Antisense oligonucleotides preferably comprise a sequence containing from about 17 to about 100 nucleotides and more preferably the antisense oligonucleotides comprise from about 18 to about 30 nucleotides expressed in the opposite orientation.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its target site, the RNA-DNA duplex activates the endogenous enzyme ribonuclease (RNase) H, which cleaves the mRNA component of the hybrid molecule.

A particularly preferred interfering nucleotide sequence is a small interfering RNA (siRNA). siRNAs mediate the post-transcriptional process of gene silencing by double stranded RNA (dsRNA) that is homologous in sequence to the silenced RNA. siRNA according to the present invention comprises a sense strand of 17-25 nucleotides complementary or homologous to a contiguous 17-25 nucleotide sequence of 14-3-3 or isoform thereof and an antisense strand of 17-25 nucleotides complementary to the sense strand. Preferably the siRNA further comprises a loop region linking the sense and the antisense strand.

A self-complementing single stranded siRNA molecule polynucleotide according to the present invention comprises a sense portion and an antisense portion connected by a loop region linker. Preferably, the loop region sequence is 4-30 nucleotides long, more preferably 5-15 nucleotides long and most preferably 8 nucleotides long. Self-complementary single stranded siRNAs form hairpin loops and are more stable than ordinary dsRNA.

Nucleic acid molecules of the present invention may be introduced into the genome or the cell of the appropriate host plant by a variety of techniques. These techniques, able to transform a wide variety of higher plant species, are well known and described in the technical and scientific literature. A variety of techniques known in the art are available for the introduction of DNA into a plant host cell. These techniques include transformation of plant cells by injection, microinjection, electroporation of DNA, PEG, use of biolistics, fusion of cells or protoplasts, and via T-DNA using *Agrobacterium tumefaciens* or *Agrobacterium rhizogenes* or other bacterial hosts, for example.

In addition, a number of non-stable transformation methods that are well known to those skilled in the art may be desirable for the present invention. Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

A person of ordinary skill in the art recognizes that after the expression cassette is stably incorporated in transgenic plants and confirmed to be operable, it can be introduced into other plants by sexual crossing. Any of a number of standard breeding techniques can be used, depending upon the species to be crossed.

The nucleic acid sequence expressing the interfering nucleotide sequence is preferably included within a vector backbone, wherein the vector backbone may be any of those typically used in the field such as plasmids, viruses, artificial chromosomes, BACs, YACs, PACs and vectors such as, for instance, bacteria-yeast shuttle vectors, lamda phage vectors, T-DNA fusion vectors and plasmid vectors.

Typically, the construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells.

Selection of an appropriate vector useful in the present invention is relatively simple, as the constraints are minimal. The minimal requirements of the vector are that the desired nucleic acid sequence be introduced in a relatively intact state. Thus, any vector which will produce a plant carrying the introduced nucleotide sequence should be sufficient. The decision as to whether to use a vector, or which vector to use, will be guided by the method of transformation selected. This determination is considered to be well with in the ordinary skill of those in the art.

The vectors typically comprise additional attached sequences which confer resistance to degradation of the nucleic acid fragment, which assist in the process of genomic integration, or which provide a means to easily select for those cells or plants which are transformed. Such sequences are advantageous and greatly decrease the difficulty of selecting useable transformed plants.

The recombinant vectors of the present invention typically comprise an expression cassette designed for initiating transcription of the desired polynucleotide sequences in plants. Other nucleotide sequences encoding additional functions may also be present in the vector, as is known in the art. For instance, in the case of Agrobacterium transformations, T-DNA sequences will also be included for subsequent transfer to plant chromosomes. For expression in plants, the recombinant expression cassette will contain, in addition to the desired polynucleotide sequence, a plant promoter region, a transcription initiation site (if the sequence to be transcribed lacks one), and a transcription termination sequence, such as SEQ ID NO: 20. Unique restriction enzyme sites at the 5' and 3' ends of the cassette are typically included to allow for easy insertion into a pre-existing vector.

The particular promoter used in the expression cassette can be varied depending on the application. Any of a number of promoters which direct transcription in plant cells is suitable. The promoter can be either constitutive or inducible. Viral promoters may include the 35S and 19S RNA promoters of cauliflower mosaic virus. (Odell et al. 1985).

A promoter which is expressed concurrently with or prior to the normal activation of the homologous endogenous sequence is generally preferred. A constitutive promoter is most preferred, such as the cauliflower mosaic virus promoter. This promoter is constitutive because its operation is relatively independent of the developmental stage of the cell in which it is contained.

In addition to a promoter sequence, the expression cassette may include a transcription termination region downstream of the structural gene to provide for efficient termination. The termination region may be obtained from the same gene as the promoter sequence or may be obtained from different genes.

The vector may also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic. In the alternative, the marker may include expressed fluorescence proteins such as YFP, green fluorescence protein, dsRED, etc.

In the case of polynucleotides used to inhibit expression of an endogenous gene, the introduced sequence also need not be perfectly identical to a sequence of the target. The introduced polynucleotide sequence will typically be at least substantially identical to the target endogenous sequence.

The introduced sequence also need not be full length relative to either the primary transcription product or fully processed mRNA. A higher sequence identity in a shorter than full length sequence compensates for a longer less identical sequence. Furthermore, the introduced sequence need not have the same intron or exon pattern, and identity of non-coding segments will be equally effective. Normally, a sequence of between about 10 nucleotides and 2000 nucleotides should be used, though a sequence of between about 100 and about 1500 nucleotides is preferred or a full length gene is especially preferred.

Two nucleic acid sequences or polypeptides are said to be "identical" if the sequence of nucleotides or amino acid residues in the two sequences is the same when aligned for maximum correspondence as described below. Optimal alignment of sequences for comparison may be conducted by a local homology algorithm or by computerized implementations of these algorithms (GAP, BESTFIT, FASTA, and TFASTA in the Wisconsin Genetics Software Package, Genetics Computer Group, 575 Science Dr., Madison, Wis.), BLAST available from NCBI or by inspection.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

Transcription of the Desired Polynucleotide Sequence in Plant Cells

The vectors described above can be microinjected directly into plant cells by use of micropipettes to mechanically transfer the recombinant DNA. (Crossway, 1985). The genetic material may also be transferred into the plant cell using polyethylene glycol (Krens, et al., 1982).

Another method of introduction of polynucleotide sequences is particle acceleration of small particles with the nucleic acid either within the matrix of small beads or particles, or on the surface (Klein, et al., 1987). Yet another method of introduction is fusion of protoplasts with other entities, such as, minicells, cells, lysosomes or other fusible lipid-surfaced bodies. (Fraley et al., 1982). The DNA may also be introduced into the plant cells by electroporation (Fromm et al., 1985). In this technique, plant protoplasts are electroporated in the presence of plasmids containing the expression cassette. Electrical impulses of high field strength reversibly permeabilize biomembranes allowing the introduction of the plasmids.

Cauliflower mosaic virus (CaMV) may be used as a vector for introducing DNA into plant cells. (Hohn et al., 1982; U.S. Pat. No. 4,407,956). In accordance with the described method, the entire CaMV vial DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

A preferred method of introducing the DNA into plant cells is to infect a plant cell with Agrobacterium tumefaciens or A. rhizogenes previously transformed with the gene. Under appropriate conditions known in the art, the transformed plant cells are grown to form shoots or roots, and develop further into plants. Preferred *Agrobacterium* strains useful in the present invention may include LBA 4404, C58C1, EHA 101, W2/73, R1601, LBA 288, GV 3850, A281, GV311 SE, A856, A136, GC3101, 1S955, and bo 42.

*Agrobacterium* is a genus in the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (Schell, J., 1987).

Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid, such vectors are typically termed binary vectors. (Hoekema et al., 1983). The transferred DNA region, can be increased in size by the insertion of heterologous DNA without its ability to be transferred being affected. A modified Ti or Ri plasmid, in which the disease-causing genes have been deleted, can be used as a vector for the transfer of the gene constructs of this invention into an appropriate plant cell.

All plant cells which can be transformed by *Agrobacterium* and from which whole plants can be regenerated can be transformed according to the present invention to produce transformed intact plants which contain the desired DNA. There are two common ways to transform plant cells with *Agrobacterium*:

co-cultivation of *Agrobacterium* with cultured isolated protoplasts, or transformation of intact cells or tissues with *Agrobacterium*.

Most dicot species can be transformed by *Agrobacterium*. All species which are a natural plant host for *Agrobacterium* are transformable in vitro.

After transformation, transformed plant cells or plants comprising the introduced DNA must be identified. A selectable marker, such as those discussed, supra, is typically used. Transformed plant cells can be selected by growing the cells on growth medium containing the appropriate antibiotic. The presence of opines can also be used if the plants are transformed with *Agrobacterium*.

After selecting the transformed cells, one can confirm expression or lack of expression of the relevant gene. Simple detection of the levels of mRNA can be achieved by well known methods in the art, such as Northern blot hybridization.

After determination that the inserted nucleotide sequence has affected the plant cell, whole plant regeneration may be desired. All plants from which protoplasts can be isolated and cultured to give whole regenerated plants can be hosts for the polynucleotide sequences of the present invention. Some suitable plants may include, but is not limited to, *Arabidopsis, Brassica, Raphanus, Sinapis, Atropa, Capsicum, Hyoscyamus, Lycopersicon, Nicotiana, Solanum, Oryza, Petunia, Digitalis, Majorana, Cichorium, Helianthus, Lactuca, Bromus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, Phaseolus, Pisum, Hordeum, Beta* and *Datura*.

Plant regeneration from cultured protoplasts is described in (Evans et al., 1983); and (Vasil I. R. ed., Vol. 1, 1984, and Vol. III, 1986). Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins Efficient regeneration will depend on the medium, on the genotype, and on the history of the culture. If these three variables are controlled, then regeneration is usually reproducible and repeatable. Regenerated plants with the desired characteristics are typically identified by determining activity of the target gene or expressed protein.

Finally, one of skill will recognize that after the expression cassette is stably incorporated in transgenic plants and confirmed to be operable, it can be introduced into other plants by sexual crossing. Any of a number of standard breeding techniques can be used, depending upon the species to be crossed.

The Invention

All plants are exposed to various abiotic and biotic stresses during their growth and development. The present invention discovered that 14-3-3 lambda in *Arabidopsis* is one of the RPW8-interacting proteins. Genetic analyses showed that a 14-3-3 lambda knockout (GF14λ-ko) line in *Arabidopsis* accession Ler background showed enhanced resistance to bacterial pathogens (*Pseudomonas syringae*) and in the mean time also showed enhanced tolerance to drought. The GF14λ-ko plants appear to have normal growth and development compared with the wild type plants. Because 14-3-3s are highly conserved regulatory proteins in all eukaryotic cells, this finding provides a novel avenue for enhancing both bacterial and drought tolerance in crop species by functionally interfering the regulatory function of plant 14-3-3 genes.

Detail mechanistic studies revealed that GF14λ is a major regulator of stomata function in *Arabidopsis*, mostly likely via interaction with plasma membrane proton pumps ($H^+$-ATPases). GF14λ knockout results in reduced stomata aperture of leaf epidermal cells, which leads to reduced transpiration rate and water loss especially during drought stress conditions. For the same reason, when spray-inoculated with bacterial pathogens (similar to natural infection), entry of bacteria via plant stomatas in GF14λ-ko plants is significantly reduced, resulting in a much milder infection. These results demonstrated that knocking out a single 14-3-3 isoform in plants could enhance drought tolerance and bacterial resistance without obvious fitness penalty under our experimental conditions.

Two approaches are discussed herein to interfere the function of 14-3-3s in relation to stomata regulation to achieve enhanced drought tolerance and bacterial resistance while minimizing any potential unwanted effect on plant productivity: (1) silencing GF14λ and its crop orthologs by nucleic acid sequence expressed by drought/bacterium-inducible and guard cell-specific promoters; (2) scavenging 14-3-3s in guard cells by expressing a short peptide (R18) with high binding affinity with 14-3-3 proteins in guard cells using drought/bacterium-inducible, guard cell-specific promoters.

The invention provides for a method for the modulation of stomata function in *Arabidopsis* or other plants. Generally, the method comprises administering to a plant a composition comprising a stomata function modulating amount of a 14-3-3 modulator.

14-3-3 modulators are used in the present methods for modulating 14-3-3 activity in plant tissues, including modulating stomata function thereby affecting 14-3-3 activity in plants and specifically guard cells.

In one preferred embodiment, the invention contemplates 14-3-3 modulators in the form of polypeptides. A polypeptide (peptide) 14-3-3 and specifically GE14λ modulator interacts with the extracellular domain of 14-3-3 and inhibits activity. In one embodiment, a polypeptide of the present invention comprises no more than about 100 amino acid residues and peptides can be linear or cyclic. Thus, it should be understood that a subject polypeptide need not be identical to the amino acid residue sequence of a 14-3-3 natural ligand, so long as it includes required binding sequences and is able to function as a 14-3-3 modulator.

A subject polypeptide includes any analog, fragment or chemical derivative of a polypeptide which is a 14-3-3 modulator. Such a polypeptide can be subject to various changes, substitutions, insertions, and deletions where such changes provide for certain advantages in its use. In this regard, a 14-3-3 modulator polypeptide of the present invention corresponds to, rather than is identical to, the sequence of the natural ligand where one or more changes are made and it retains the ability to function as a 14-3-3 modulator in one or more of the assays.

Thus, an inhibiting polypeptide can be in any of a variety of forms of peptide derivatives, that include amides, conjugates with proteins, cyclized peptides, polymerized peptides, analogs, fragments, chemically modified peptides, and the like derivatives.

An inhibiting peptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv Enzymol, 32:221 96, 1969; Fields et al., Int. J. Peptide Protein Res., 35:161 214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

In the alternative a modulating protein can be expressed within plants cell and expressed during times of stress by promoters that are activation during such stress. The DNA encoding such protein is introduced by recombinant methods included the use of a vector, as described above. In this vector, it is understood that the DNA coding sequences to be expressed, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter.

As is known in the art, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region or a promoter region.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

For introduction of, for example, the gene to be expressed, it is proposed that one will desire to preferably employ a vector construct that will deliver the desired gene to the plants cells. This will, of course, generally require that the construct be delivered to the targeted cells, for example, guard cells of the plant. It is proposed that this may be achieved by introduction of the desired gene through the use of a viral vector to carry the sequence to efficiently infect the cells. In the alternative a plasmid incorporating the necessary nucleotide sequence may be used to transfect a plant cell.

Appropriate regulatory sequences can be inserted into the vectors of the invention using methods known to those skilled in the art, for example, methods discussed in Molecular Cloning: A Laboratory Manual, Sambrook et al., eds., Cold Spring Harbor Laboratory, 2nd Edition, Cold Spring Harbor, N.Y., 1989.

EXAMPLES

Example 1

14-3-3λ-Deficient Mutants Showed Enhanced Resistance to *Pseudomonas syringae* When Spray-Inoculated An *Arabidopsis* 14-3-3 protein (the lambda isoform; At5g10450; GF14λ) is identified as a putative interacting partner of RPW8.2 which is a powdery mildew resistance protein in *Arabidopsis* (Xiao et al., 2001). In order to characterize the function of GF14λ (At5g10450) in plant defense, one GF14λ knockout (GF14λko) line (CSHL_ET5632 in Landsberg erecta (Ler) background) was characterized in response to pathogen infections. The T-DNA was inserted in 110 bp downstream of the ATG start codon. RT-PCR (data not shown) and Northern blot analyses showed that GF14λ expression was knocked out in this mutant line (FIG. 1A). There was no detectable difference between the mutant and the wild type in plant growth and development measured by leaf size and fresh weight per fully expanded mature leaf, and seed number per silique and seed weight per 50 siliques (FIG. 1B-E).

Figure 2:
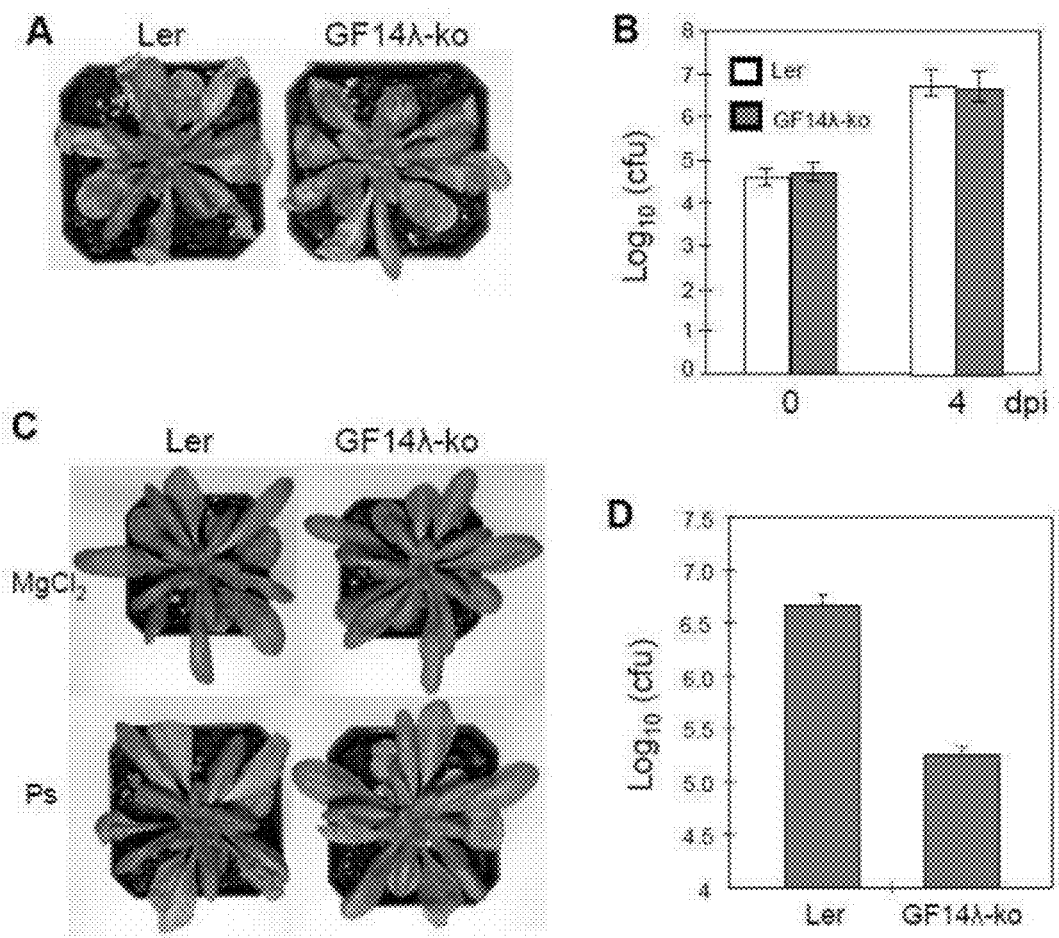

When the mutant plants and Landsberg erecta (Ler) wild type were inoculated with a virulent *P. syringae* strain pv. *by* injecting the bacteria into the leaf tissues, no obvious difference in disease severity was observed between the mutant and the wild type (FIG. 2 A&B). However, when the bacterial pathogen was spray-inoculated on the leaf surface (which is more similar to natural infection), significant differences both in terms of leaf chlorotic symptoms and growth of the bacterium inside the leaf tissues were observed (FIGS. 2C&D). Similar results were obtained from tests with a different virulent bacterial strain *P. syringae* pv. *maculicola* ES4326 (data not shown).

To confirm if the enhanced resistance to *P. syringae* is indeed caused by the GF14λ knockout mutation, a GF1λ transgene under control of the 35S promoter was introduced into GF14λ-ko mutant background. The transgenic plants restored normal disease susceptibility to *P. syringae* when spray-inoculated (data not shown), suggesting that GF14λ negatively regulates plant defense against bacterial pathogens in *Arabidopsis*.

Example 2

Figure 3:
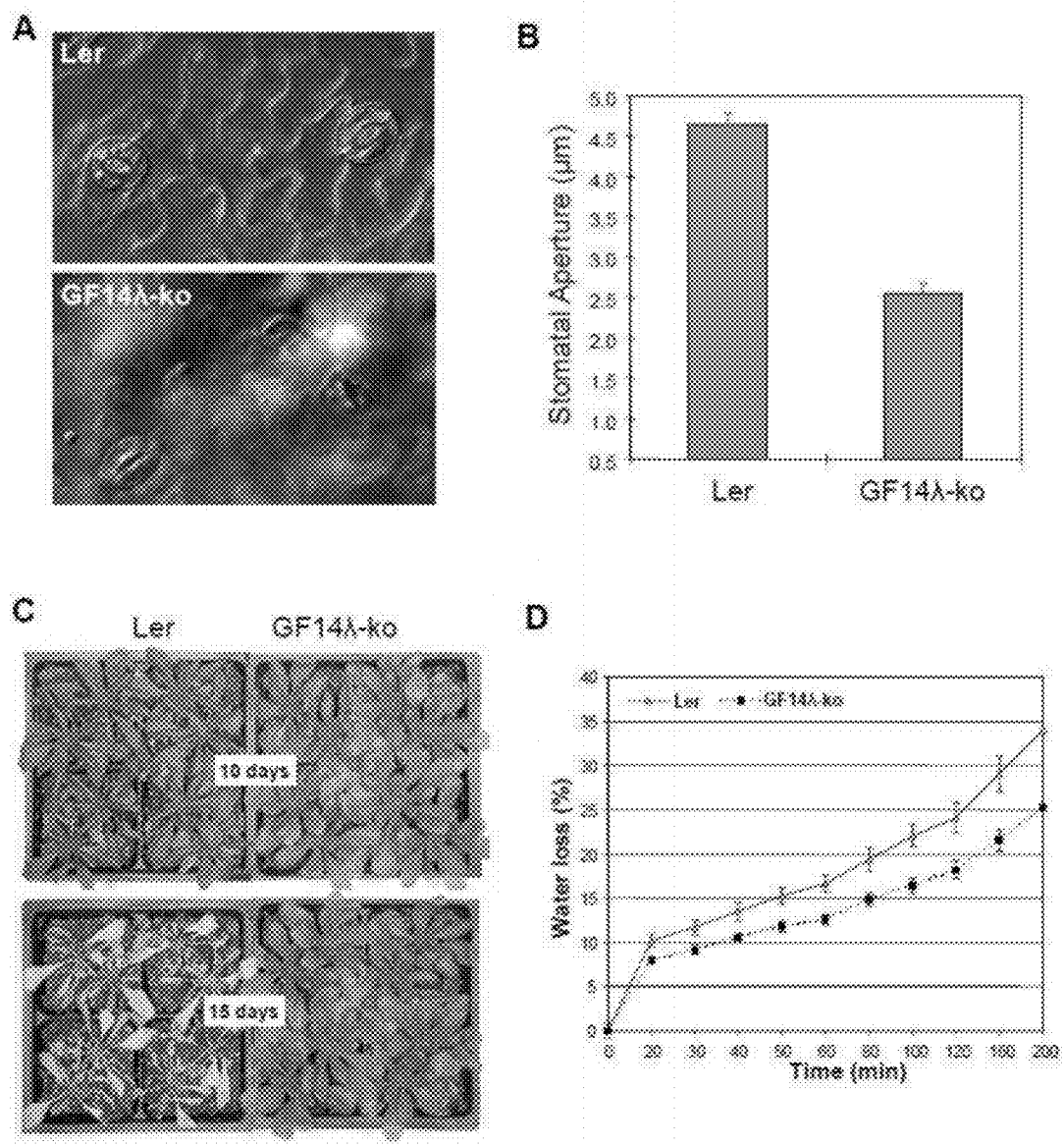

Enhance Bacterial Resistance of GF14λ Knockout Plants is Caused by Reduced Bacterium Entry Due to Reduced Stomatal Aperture To find out why the GF14λ knockout mutant is more resistant than the wild-type to spray-inoculated bacterial pathogens, the leaf surface structures of the GF14λ -ko and Ler were compared and it was found that the stomatal aperture of the guard cells in GF14λ-ko leaves was only about half of that in Ler (FIG. 3 A&B). This finding was very interesting though not entirely unexpected because 14-3-3s have been shown to interact with the $H^+$-ATPases in guard cells in broad bean to activate the proton pump in response to blue light (Kinoshita and Shimazaki, 1999; Kinoshita et al., 2003). However, genetic evidence for a role of 14-3-3s in control of stomata open/closure has not been provided heretofore. These findings provide the first piece of solid genetic evidence for a critical role of 14-3-3s in control of stomata open, which in turn provides a logical explanation to the reduced disease symptom and bacterial growth in GF14λ-ko plants when the pathogen was spray-inoculated on the leaf surface (because fewer bacteria could get into the leaf tissue in the first place).

Example 3

GF14λ-ko Mutant Plants were More Tolerant to Drought

Because the stomatal aperture in GF14λ-ko plants is reduced by half, it was reasoned that the mutant plants may be more tolerant to drought stress due to less water loss. In several independent experiments, four week-old GF14λ-ko and Ler plants were kept in a growth chamber (set to 8 hrs light/16 hrs dark, ~150 $\mu mol \cdot m^{-2} \cdot sec^{-1}$ light intensity, 28° C., and 50% relative humidity), without water supply for 14 days. Ler plants started to show leaf-wilting from day 8-10 on and all of them suffered irreversible fatal damage at day 14. By contrast, all GF14λ-ko showed no or little wilting at day 8-10 and showed some wilting in day 12-14, but all of them recovered one day after water supply on day 14. To see if the enhanced drought tolerance of GF14λ-ko plants was indeed due to reduced water loss during the drought stress, fully-expanded mature leaves of 5 week-old plants of Ler and GF14λ-ko were detached and kept under the same conditions as for the whole plant-treatment described above. Notably, there were no significant differences in leaf area and fresh weight between the mature leaves from Ler and GF14λ-ko plants at the starting point of the experiment (data not shown). However, when water-loss in these leaves was measured at 10 time points over a period of 200 minutes, it was found that water-loss in the leaves from GF14λ-ko plants was 5 to 9% less than that from wild-type (FIGS. 3C&D), further demonstrating that GF14λ-ko plants were more tolerant to drought stress owing to their reduced stomata aperture (FIG. 3 A&B).

Two GF14λ T-DNA knockdown mutants in *Arabidopsis* accession Col-0 have also been characterized. Phenotypic and genetic analyses showed that these two knockdown mutants exhibited similar, albeit slightly weaker, enhanced drought tolerance and bacterial resistance compared with the Col-0 wild-type (data not shown).

Silencing by RNAi of the likely functional GF14λ orthologs in tobacco, tomato and poplar is conducted to show that similar enhanced drought tolerance and bacterial resistance can be achieved. RNAi constructs under control of a synthetic drought-inducible, guard cell-specific promoter DGP1 (Li et al., 2005) are used to transform tobacco, tomato and poplar to generate more drought tolerant plants. To avoid the GMO issue, EMS or radiation-mutagenesis of target crop plants such as tomato and corn is conducted to determine loss-of-function or dominant-negative mutations in the relevant 14-3-3 genes. These non-transgenic mutants are developed as drought-tolerant and bacterium-resistant cultivars or used as breeding materials for creating drought-tolerant and bacterium-resistant cultivars.

The 14-3-3-binding R18 peptide (PHCVPRDLSWLDLE-ANMCLP) (SEQ ID NO: 1) (Wang et al., 1999) has been shown to be able to scavenge 14-3-3s and inhibit their functions in animals (Dong et al., 2007; Dong et al., 2008) and affect subcellular localization of *Arabidopsis* 14-3-3s (Paul et al., 2005). Thus the possibility of stably expressing R18 (fused to DsRed (SEQ ID NO: 4) so that its expression can be monitored) in *Arabidopsis* was explored to assess if R18 expression interfered with the functions of 14-3-3s including GF14%. If bacterial resistance is the major breeding target, the RNA1 or R18 fusion gene constructs discussed above are put under control of a bacterial pathogen-inducible promoter such as the promoter of DAPP1 to create desirable transgenics. DAPP1 is an *Arabidopsis* defense-related gene that is expressed in plant leaf tissue as soon as 1 hr after inoculation with a virulent strain of *P. syringae*.

Example 4

Figure 4:
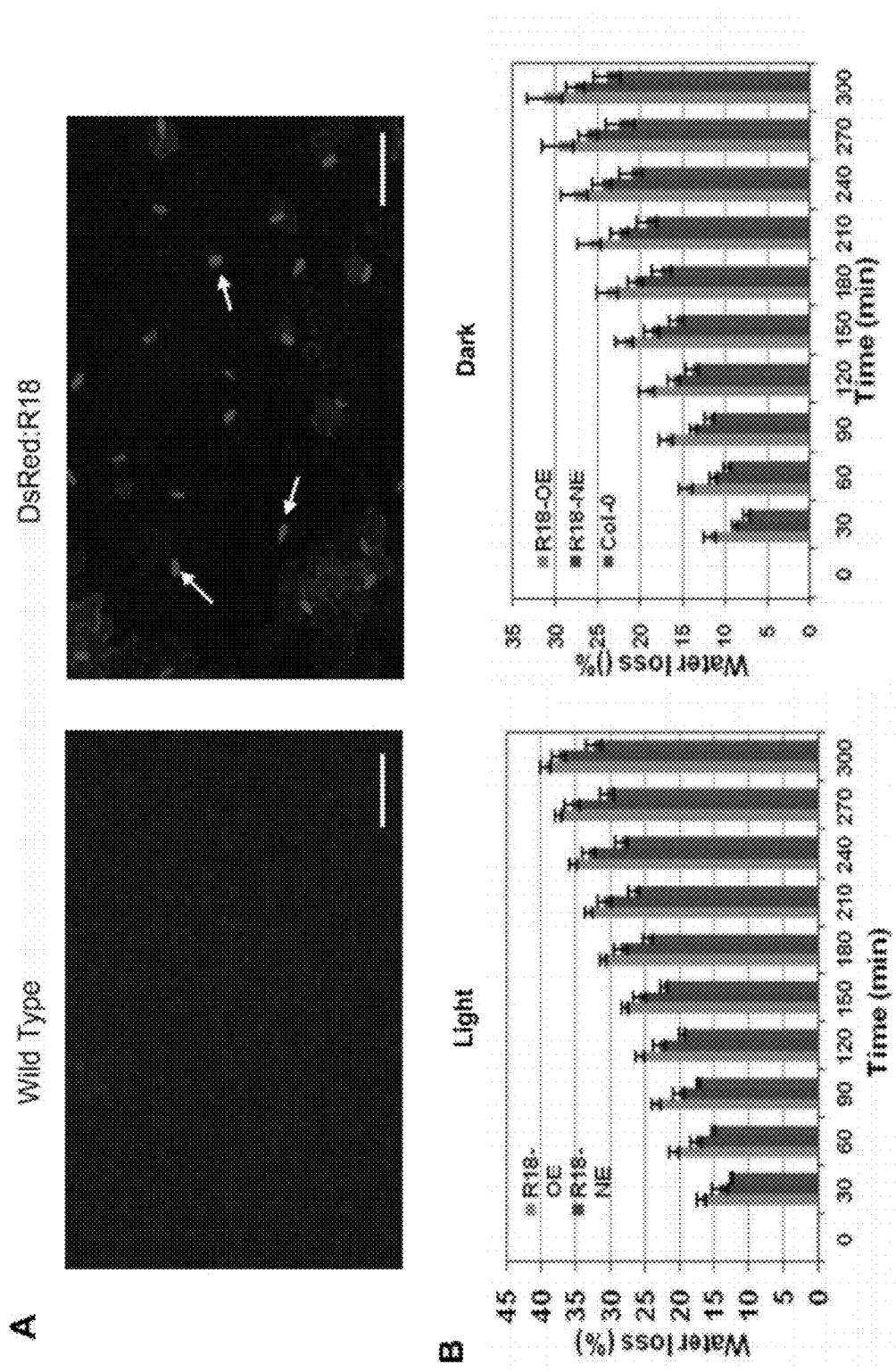

*Arabidopsis* Plants Expressing the R18 Short Peptide are More Drought Sensitive The 14-3-3-binding short peptide R18 (SEQ ID NO: 1) encoded by SEQ ID NO: 3 [Petrosa and Wang 1999] was fused to DsRed (SEQ ID NO 4, encoded by SEQ ID NO: 5) and the chimeric gene was expressed from the 35S promoter (SEQ ID NO: 6) in *Arabidopsis* accession Col-0. It was found that DsRed:R18 is more preferentially expressed in guard cells in most transgenic lines examined (FIG. 4A). Two independent homozygous transgenic lines were evaluated for drought tolerance. Surprisingly, the transgenic plants were significantly more drought sensitive compared to wild-type Col-0 plants (FIG. 4B). Considering that a fungal toxin, fusicoccin, binds 14-3-3 (in one of its two binding pockets) and stabilizes the binding of the C-terminus of $H^+$-ATPase to the other binding pocket of 14-3-3, thereby irreversibly activating the latter, resulting in constant stomatal opening and eventual weathering of leaves infected by the fungal pathogen [Korthout, Jahn, Baunsgaard, Kinoshits 2002, Fuglsang and Ottmann], this unexpected result indicated that the binding site of R18 in 14-3-3 is the same as fusicoccin and that R18-14-3-3 binding stabilized 14-3-3-$H^+$-ATPase interaction, resulting in enhanced drought sensitivity.

Example 5

Figure 5:
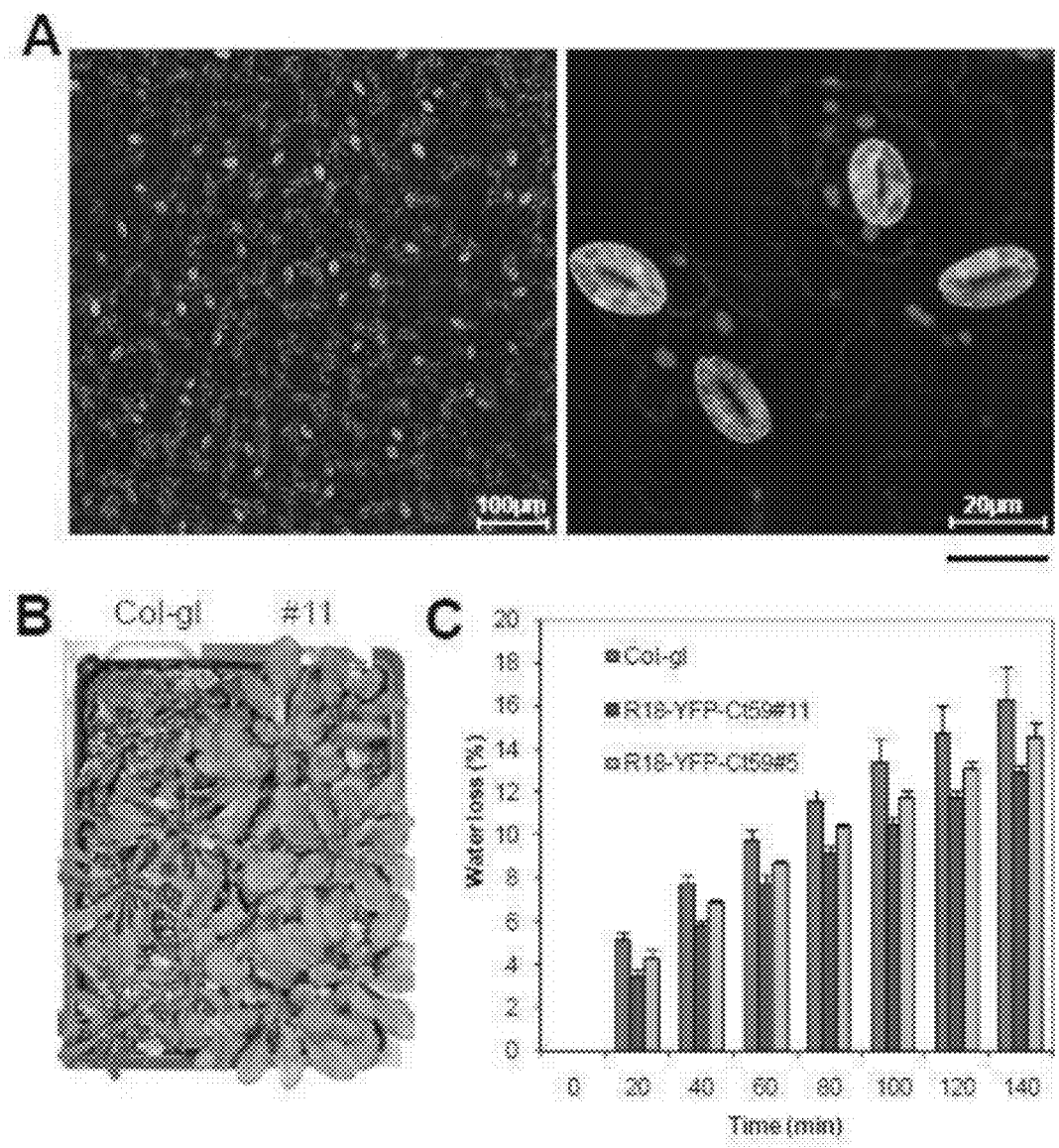

*Arabidopsis* Plants Expressing a 14-3-3 Trap Protein R18:YFP:Ct59 are More Drought Tolerant Based on the above finding, a DNA construct was made to express a protein that contains R18 (SEQ ID NO: 1) and the C-terminus of $H^+$-ATPase (SEQ ID NO: 2), noting that this chimeric protein binds 14-3-3 in two separate binding sites, effectively sequestering it from the endogenous $H^+$-ATPase at the plasma membrane. The R18 is translationally fused with YFP (to provide a spacer aid visual examination of the fusion protein), and then with the last 59 amino acids of $H^+$-ATPase (designated Ct59<SEQ ID NO: 2)) of Arabidopsis $H^+$-ATPase (At4g30190). The penultimate threonine (T) of Ct59 was mutated to aspartic acid (D) to mimic constitutive phosphorylation, enabling interaction between Ct59 and 14-3-3. The DNA construct was placed under control of a synthetic promoter containing elements from drought inducible and guard cell-specific promoters (designated DG), or 35S plus this synthetic promoter (35S-DG). Transgenic plants expressing DG::R18-YFP-Ct59 or 35S-DG::R18-YFP-Ct59 showed expression of the fusion protein predominantly in guard cells (FIG. 5A). More significantly, these transgenic plants showed significantly enhanced drought tolerance than Col-gl wild-type plants (FIG. 5B&C). To date, no significant difference has been observed in plant growth and development between transgenic plants and Col-0, suggesting that this 14-3-3 sequestration strategy can effectively enhance drought tolerance with minimal negative effect on other traits of plants. Because both 14-3-3s and Ht ATPases are highly conserved in all plants, the same DNA construct, DG::R18-YFP-Ct59 or 35S-DG::R18-YFP-Ct59, can be used to generate drought-tolerant cultivars for any crop plant.

DG promoter is a combination of a drought-responsive element (DiP): 253 bp from −443 to −182 bp upstream of the ATG start codon of rd29A (AY973635) from *Arabidopsis*, which contains 2×TACCGACAT (SEQ ID NO: 14) and a guard-cell-specific promoter element (GcP): 241 bp from −241 to −1 bp upstream of the ATG start codon of Kst1 (X79779) from potato, which contains 2×TAAAG (SEQ ID NO: 15).

Transgenic plants expressing DG::R18-YFP-Ct59 or 35S-DG::R18-YFP-Ct59 showed expression of the fusion protein predominantly in guard cells (FIG. 5A). More significantly, these transgenic plants showed significantly enhanced drought tolerance than Col-g1 wild-type plants (FIGS. 5B&C). To date, no significant difference has been observed in plant growth and development between transgenic plants and Col-0, suggesting that this 14-3-3 sequestration strategy can effectively enhance drought tolerance with minimal negative effect on other traits of plants. Because both 14-3-3s and $H^+$-ATPases are highly conserved in all plants, the same DNA construct, DG::R18-YFP-Ct59 or 35S-DG::R18-YFP-Ct59, can be used to generate drought-tolerant cultivars for any crop plant.

Example 6

Using R18:YFP:Ct59 or R18:YFP:X (X Represent any C-Terminal 14-3-3 Binding Site of Yeasts, Plants or Animals 14-3-3 Binding Proteins) as a 14-3-3 Trap to Sequester 14-3-3 from its Endogenous Client Proteins in a Tissue/Organ-Specific Manner to Intervene Cellular Processes Notably, because 14-3-3 is conserved from yeast to plants to human, there are wide potential applications for R18:YFP:Ct59 such as described in SEQ ID NO: 10 and encoded by SEQ ID NO: 11 or R18:YFP:X in (i) studying cellular functions and signaling pathways of various 14-3-3 client proteins; (ii) treating diseases where 14-3-3 client proteins play essential roles. For example, Dong et al. (2007) reported that R18 was only able to dissociate proapoptotic protein FOXO3a, but not BAD, from 14-3-3 binding and induced apoptosis partially through liberation and reactivation of FOXO3a. However, the use of R18:YFP:Ct59 or R18:YFP:X should able to dissociate both FOXO3a and BAD (theoretically all proteins that bind 14-3-3 via the same sites as R18 and Ct59), therefore inducing apoptosis more effectively of cancer cells of myeloid leukemia and/or lymphoma.

Example 7

Figure 6:

*Arabidopsis* Plants Transgenic for 35S-DG::R18-YFP-Ct59 Showed Normal Growth and Development Based on T2 progenies of 6 independent transgenic lines (>24 plant for each line) expressing R18:YFP:Ct59 under growth chamber conditions, it was found that there was no significant difference in growth and development between the transgenic plants and the wild-type control. Three maturing representative plants are shown in FIG. 6.

Example 8

R18, Ct59, and R18:Ct59 Interact with 14-3-3s in Planta

The testing results of this example show that (i) both R18 and Ct59 interact with 14-3-3s individually, (ii) R18 and Ct59 simultaneously interact with 14-3-3s when they are both expressed in the same cell in trans (from two different constructs) or in cis (as two separate domains of the same fusion protein); and (iii) R18 may stabilize or strengthen Ct59's interaction with 14-3-3s. The bimolecular fluorescence complementation (BiFC) approach was used to show these results.

Specifically, several construct were generated and in-frame translationally fused including (i) gene encoding the protein 14-3-3λ (SEQ ID NO: 12) with the N-terminal portion of YFP (YFPn) to make 14λ-YFPn or with the C-terminal portion (154-240 amino acids) of YFP (YFPc) to make 14λ-YFPc, (ii) R18 with YFPn to make R18-YFPn, (iii) YFPc with Ct59 to make YFPc-Ct59, and (iv) YFPc with R18:Ct59 (Note in this case, a linker sequence encoding GGSGGGGG (SEQ ID NO: 17) is placed between YFPc and R18, and between R18 and Ct59, to enable binding flexibility of R18 and Ct59) to make YFPc-R18-Ct59. Notably it is possible to use SEQ ID NO: 18 which provides a nucleotide sequence that includes a synthetic DNA sequence encoding 20 amino acids of SEQ ID NO: 1 plus the ATG start codon and the linking sequence encoding SEQ ID NO: 17. All of these constructs were cloned into the binary vector pCX—SN (FJ905214) under control of the 35S viral promoter (SEQ ID NO: 6), and then the recombinant plasmids were introduced into *Agrobacterium tumefaciens* GV3101. The DNA constructs were then expressed in plant cells using two of the following approaches.

Figure 7:
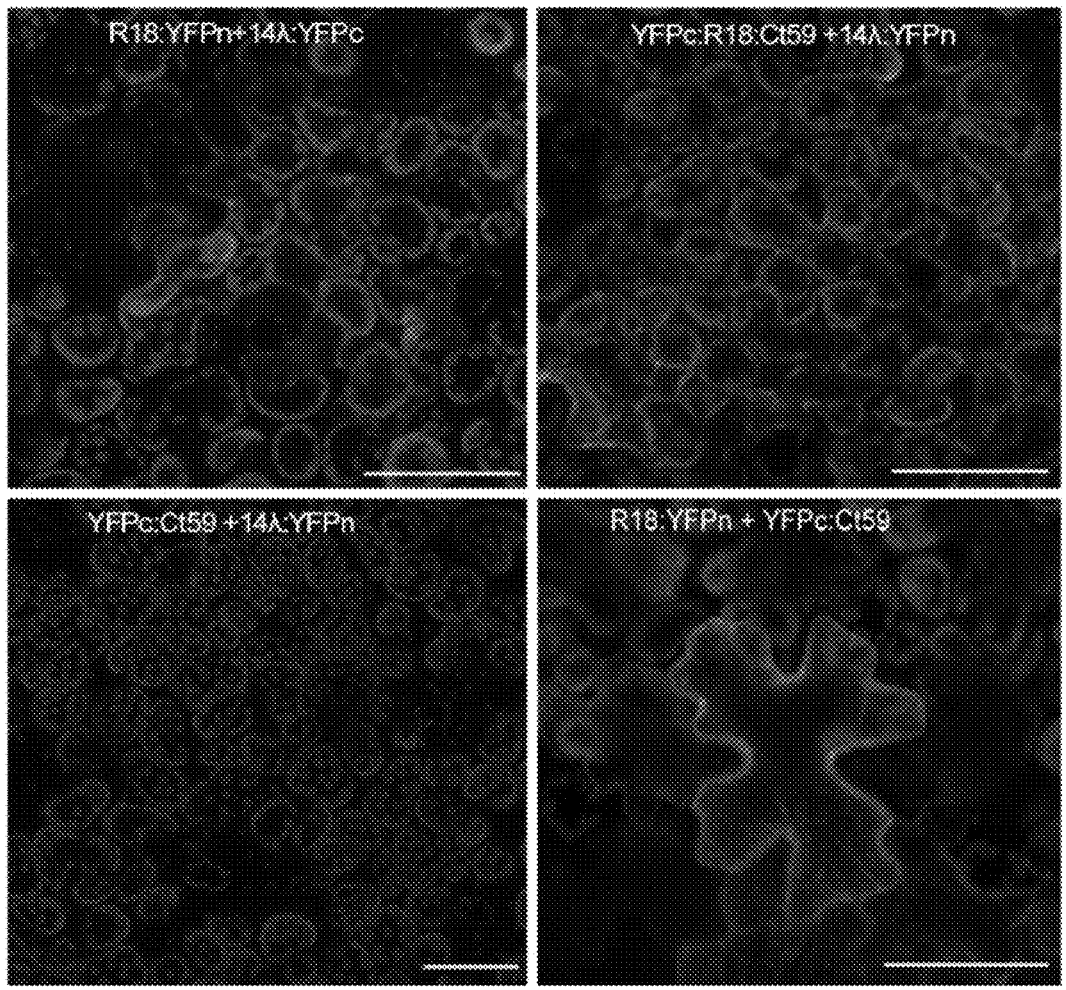

Transient expression. Agrobacterial cells ($OD_{600}$=0.2-0.5) carrying the indicated constructs were infiltrated to *Nicotiana benthamiana* leaves to enable transient expression of the fusion proteins. Infiltrated leaf sections were examined under an epifluorescent or confocal microscope two days after infiltration. Detection of YFP signal as a result of reconstitution of the YFP protein would indicate the two fusion proteins under test physically interact. As shown in FIG. 7, R18:YFPn indeed did interact with 14%:YFPc, and YFPc:R18:Ct59 interacted with 14%:YFPn. Interestingly, the pattern of reconstituted YFP from R18:YFPn+14λ:YFPc was somewhat different from that of YFPc:R18:Ct59+14X:YFPn, with the former being found in both mesophyll and epidermal cells, and the latter primarily in epidermal cells (FIG. 7). However, there was no observing of the YFP signal from co-expression of YFPc:Ct59 and 14λ:YFPn. It is possible that the C-terminus (—YDV-COOH) of Ct59 may only weakly interact with 14λ, which may not be detectable by BiFC in *N. benthamiana*, or there is no interaction due to Ct59's lacking of the normal penultimate threonine that is phosphorylated under light in the wild-type H+-ATPase. When R18:YFPn and YFPc:Ct59 were co-expressed, YFP signal was also observed, indicating R18 and Ct59 can simultaneously bind endogenous 14-3-3s of *N. benthamiana*, thereby bring the N and C domains of YFP together to produce YFP signal. When R18:YFPn, YFPc:Ct59 and 14λ:YFPn were co-expressed, YFP signal was readily detectable (not shown). Combined, these results show that R18, R18-Ct59 and R18+Ct59 can bind 14-3-3s, and also show that R18's binding to 14-3-3s enhances Ct59's binding to 14-3-3s.

Stable expression. The DNA constructs relevant to BiFC were introduced into *Arabidopsis* by *Agrobacterium*-mediated co-transformation. Interactions between R18:YFPn and 14%:YFPc, YFPc:R18:Ct59 and 14λ:YFPn, R18:YFPn and YFPc:Ct59 (via co-binding to the endogenous 14-3-3 proteins), and between YFPc:Ct59 and 14λ:YFPn were demonstrated in stable transgenic *Arabidopsis* by BiFC (FIG. 8). Importantly, while YFP signal generated as a result of BiFC was detected for all the four combinations (Note YFP signal was not detectable for the last combination in *N. benthamiana* by transient expression), YFP signal in plants co-expressing YFPc:Ct59 and 14λ:YFPn is the weakest, which is in sharp contrast to the strong YFP signal in plants co-expressing the other three sets of constructs, particularly the YFPc:R18:Ct59-14λ:YFPn combination (FIG. 8). These results validated those from transient expression in *N. benthamiana* using Agroinfiltration (FIG. 7). Taken together, the BiFC data suggest that (i) R18 and Ct59, when expressed in cis or in trans, can simultaneously bind to 14-3-3 proteins and (ii) R18's binding unexpectedly and surprisingly enhances the interaction between Ct59 and 14-3-3, which provide the rationale for effective sequestration of 14-3-3s by R18:YFP:Ct59 (SEQ ID NO: 10 and sequences having about 90% identity thereof with the same functional activity of sequestering 14-3-3s).

Potential impact and expected outcomes: Billions of acres of plants around the globe suffer from drought every year. In addition, one major obstacle in making biofuel cost effective is water limitation. Thus generation of water conserving and drought-tolerant food and feedstock crop plants is highly desirable for sustainable modern agriculture. The results shown herein provide for a novel strategy to enhance drought tolerance of crop plants via direct control of stomatal opening/closure. Because 14-3-3s are highly conserved in all plants, the same one-for-all DNA construct, such as SEQ ID NO: 10 and sequences References The references cited herein are incorporated by reference herein for all purposes.

Baunsgaard, L., et al., The 14-3-3 proteins associate with the plant plasma membrane H(+)-ATPase to generate a fusicoccin binding complex and a fusicoccin responsive system. Plant J, 1998. 13(5): p. 661-71.

Buckley, T. N. (2005). The control of stomata by water balance. New Phytol 168, 275-292.

Crossway, A.; Oakes, J.; Irvine, J.; Ward, B.; Knauf, V.; Shewmaker, C. K. 1986. Integration of foreign DNA following microinjection of tobacco meophyll photoplasts. *Mol. Gen. Genet.*, 202: 179-85.

Dong, S., Kang, S., Lonial, S., Khoury, H.J., Viallet, J., and Chen, J. (2008). Targeting 14-3-3 sensitizes native and mutant BCR-ABL to inhibition with U0126, rapamycin and Bcl-2 inhibitor GX15-070. Leukemia 22, 572-577.

Dong, S., Kang, S., Gu, T. L., Kardar, S., Fu, H., Lonial, S., Khoury, H. J., Khuri, F., and Chen, J. (2007). 14-3-3 Integrates prosurvival signals mediated by the AKT and MAPK pathways in ZNF198-FGFR1-transformed hematopoietic cells. Blood 110, 360-369.

Fraley R. T., Dellaporta S. L., and Papahadjopoulos D. (1982) Liposome-Mediated Delivery of Tobacco Mosaic Virus RNA into Tobacco Protoplasts: A Sensitive Assay for Monitoring Liposome-Protoplast Interactions. *Proc. Natl. Acad. Sci. USA*, 79(6): 1859-1863.

Fromm M., Taylor L. P., and Walbot V. (1985) Expression of genes transferred into monocot and dicot plant cells by electroporation. *Proc. Natl. Acad. Sci. USA*, 82(17):5824-5828.

Fuglsang, A. T., et al., (2003) The binding site for regulatory 14-3-3 protein in plant plasma membrane H+-ATPase: involvement of a region promoting phosphorylation-independent interaction in addition to the phosphorylation-dependent C-terminal end. J Biol Chem, 278(43): p. 42266-72.

Hashimoto, M., Negi, J., Young, J., Israelsson, M., Schroeder, J. I., and Iba, K. (2006). *Arabidopsis* HT1 kinase controls stomatal movements in response to CO2. Nat Cell Biol 8, 391-397.

Jahn, T., et al., (1997) The 14-3-3 protein interacts directly with the C-terminal region of the plant plasma membrane H(+)-ATPase. Plant Cell, 9(10): p. 1805-14.

Kinoshita, T., and Shimazaki, K. (1999). Blue light activates the plasma membrane H(+)-ATPase by phosphorylation of the C-terminus in stomatal guard cells. Embo J 18, 5548-5558.

Kinoshita, T., Emi, T., Tominaga, M., Sakamoto, K., Shigenaga, A., Doi, M., and Shimazaki, K. (2003). Blue-light- and phosphorylation-dependent binding of a 14-3-3 protein to phototropins in stomatal guard cells of broad bean. Plant Physiol 133, 1453-1463.

Kinoshita, T. and K. Shimazaki, (2002) Biochemical evidence for the requirement of 14-3-3 protein binding in activation of the guard-cell plasma membrane H+-ATPase by blue light. Plant Cell Physiol, 43(11): p. 1359-65.

Klein T. M., Wolf E. D., Wu R. and Sanford J. C. (1987) High-velocity microprojectiles for delivering nucleic acids into living cells. *Nature*, 327(6117):70-73.

Korthout, H. A. and H. A. de Boer, (1994) A fusicoccin binding protein belongs to the family of 14-3-3 brain protein homologs. Plant Cell, 6(11): p. 1681-92.

Krens F. A, Molendijk L., Wullems G. J. and Schilperoort R. A. (1982) In vitro transformation of plant protoplasts with Ti-plasmid DNA. *Nature,* 296(5852):72-74.

Li, J., Gong, X., Lin, H., Song, Q., Chen, J., and Wang, X. (2005). DGP1, a drought-induced guard cell-specific promoter and its function analysis in tobacco plants. Sci China C Life Sci 48, 181-186.

Melotto, M., Underwood, W., Koczan, J., Nomura, K., and He, S. Y. (2006). Plant stomata function in innate immunity against bacterial invasion. Cell 126, 969-980.

Odell J. T., Nagy F. and Chua N.-H. (1985). Identification of DNA sequences required for activity of the cauliflower mosaic virus 35S promoter. *Nature.* 313(6005):810-812.

Ottmann, C., et al., (2007) Structure of a 14-3-3 coordinated hexamer of the plant plasma membrane H+-ATPase by combining X-ray crystallography and electron cryomicroscopy. Mol Cell, 25(3): p. 427-40.

Paul, A. L., Sehnke, P.C., and Ferl, R. J. (2005). Isoform-specific subcellular localization among 14-3-3 proteins in *Arabidopsis* seems to be driven by client interactions. Mol Biol Cell 16, 1735-1743.

Petosa, C., et al., (1998) 14-3-3zeta binds a phosphorylated Raf peptide and an unphosphorylated peptide via its conserved amphipathic groove. J Biol Chem, 273(26): p. 16305-10.

Schell J., (1987) Transgenic plants as tools to study the molecular organization of plant genes. *Science,* 237(4819): 1176-1183.

Shimazaki, K., Doi, M., Assmann, S. M., and Kinoshita, T. (2007). Light regulation of stomatal movement. Annu Rev Plant Biol 58, 2 19-247.

Wang, B., Yang, H., Liu, Y. C., Jelinek, T., Zhang, L., Ruoslahti, E., and Fu, H. (1999). Isolation of high-affinity peptide antagonists of 14-3-3 proteins by phage display. Biochemistry 38, 12499-12504.

Xiao, S., Ellwood, S., Calis, O., Patrick, E., Li, T., Coleman, M., and Turner, J. G. (2001). Broad-spectrum mildew resistance in *Arabidopsis thaliana* mediated by RPW8. Science 291, 118-120.

---

That which is claimed is:

1. A DNA construct comprising, a nucleotide sequence encoding for SEQ ID NO: 1 and a nucleotide sequence encoding the C-terminus of a proton pump ($H^+$-ATPase), wherein the C-terminus of a proton pump consists of SEQ ID NO: 2, wherein the expressed protein interferes with the binding of 14-3-3 to the C-terminus of the proton pump ($H^+$-ATPase) and the activation of the proton pump thereby reducing the induction of the stomatal opening.

2. The DNA construct of claim 1, further comprising a nucleotide sequence encoding a visual marker for expression.

3. The DNA construct of claim 1, wherein the visual marker is yellow fluorescence protein.

4. A method of enhancing drought tolerance and bacterial resistance of crop species, the method comprising the steps of:

(a) transforming plant cells with the DNA construct of claim 1 operably linked to a promoter;

(b) regenerating transgenic plants from said transformed plant cells; and (c) selecting a transformed plant from said transgenic plants which exhibits increase in tolerance to drought stress as compared to an untransformed plant o the same species.

5. The method of claim 4, further comprising transforming the plant cells with a marker for identifying the transformed plant.

6. The method of claim 5, wherein the nucleotide sequence of the DNA construct encodes the amino acid sequence set forth in SEQ ID NO: 10.

7. The method of claim 4 wherein the nucleotide sequence of the promoter is selected from the group consisting of DIP (SEQ ID NO: 14), GcP (SEQ ID NO: 15), 35S of cauliflower virus (SEQ ID NO: 6) or combinations thereof.

8. A transgenic plant cell transformed with the DNA construct according to claim 1 and wherein the transgenic plant cell exhibits increased drought tolerance upon expression of the interfering protein in the transformed plant cell as compared to a control plant cell of the same species lacking the DNA construct.

9. The transgenic plant cell of claim 8, wherein the DNA construct further comprising a nucleotide sequence encoding a visual marker for expression.

10. The transgenic plant cell of claim 8, wherein the DNA construct further comprising a promoter selected from the group consisting of DIP (SEQ ID NO: 14), GcP (SEQ ID NO: 15), 35S of cauliflower virus (SEQ ID NO: 6) or combinations thereof.

11. A transformed plant regenerated from the transgenic plant cell of claim 8, and wherein the regenerated transformed plant has increased drought tolerance as compared to a control plant of the same species lacking the DNA construct.

12. The transformed plant of claim 11, comprising vegetative tissue, wherein the vegetative tissue comprises the DNA construct of claim 1.

13. The DNA construct of claim 1, wherein the nucleotide sequence encoding for SEQ ID NO: 1 is SEQ ID NO: 3 and wherein the nucleotide sequence encoding for the amino acid sequence consisting of SEQ ID NO: 2 is SEQ ID NO: 7.

14. The DNA construct of claim 13, further comprising a promoter nucleotide sequence selected from the group consisting of DIP (SEQ ID NO: 14), GcP (SEQ ID NO: 15), 35S of cauliflower virus (SEQ ID NO: 6) or combinations thereof.

15. The DNA construct of claim 14, further comprising a nucleotide sequence encoding a fluorescence marker.

16. A vector comprising the DNA construct of claim 15.

* * * * *